US012661370B2

(12) United States Patent
Marcuccio et al.

(10) Patent No.: US 12,661,370 B2
(45) Date of Patent: Jun. 23, 2026

(54) AMINO ACID SALTS OF NICOTINIC ACID RIBOSIDES AS ANTI-AGING AGENTS

(71) Applicants: Jumpstart Fertility Pty Ltd, Coogee (AU); Life Biosciences, Inc., Boston, MA (US)

(72) Inventors: Sebastian Mario Marcuccio, Endeavour Hills (AU); Rohan David Joyce, Noble Park (AU); Michel Wathier, Allston, MA (US); Roland Dolle, Boston, MA (US); Simon Tucker, Coogee (AU)

(73) Assignees: Jumpstart Fertility Pty Ltd (AU); Life Biosciences, Inc., Boston, MA (US)

( * ) Notice: Subject to any disclaimer, the term of this patent is extended or adjusted under 35 U.S.C. 154(b) by 1002 days.

(21) Appl. No.: 17/057,380

(22) PCT Filed: May 22, 2019

(86) PCT No.: PCT/US2019/033494
§ 371 (c)(1),
(2) Date: Nov. 20, 2020

(87) PCT Pub. No.: WO2019/226755
PCT Pub. Date: Nov. 28, 2019

(65) Prior Publication Data

US 2021/0196742 A1 Jul. 1, 2021

Related U.S. Application Data

(60) Provisional application No. 62/675,065, filed on May 22, 2018.

(51) Int. Cl.
*A61K 31/7084* (2006.01)
*C12N 5/075* (2010.01)

(52) U.S. Cl.
CPC ........ *A61K 31/7084* (2013.01); *C12N 5/0609* (2013.01); *C12N 2500/05* (2013.01); *C12N 2501/10* (2013.01); *C12N 2501/999* (2013.01)

(58) Field of Classification Search
CPC .......................... A61K 31/7084; C07H 19/048
See application file for complete search history.

(56) References Cited

U.S. PATENT DOCUMENTS

| | | | |
|---|---|---|---|
| 5,157,022 | A | 10/1992 | Barbul |
| 10,000,519 | B2 | 6/2018 | Migaud et al. |
| 10,183,036 | B2 | 1/2019 | Dellinger et al. |
| 10,280,190 | B2 | 5/2019 | Dellinger et al. |
| 10,485,814 | B2 | 11/2019 | Szczepankiewicz et al. |
| 2013/0059384 | A1 | 3/2013 | Tilly et al. |
| 2021/0309685 | A1 | 10/2021 | Marcuccio et al. |

FOREIGN PATENT DOCUMENTS

| | | | |
|---|---|---|---|
| GB | 925567 | A | 5/1963 |
| WO | WO 2015/186114 | A1 | 12/2015 |
| WO | 2016149395 | A1 | 9/2016 |
| WO | WO 2017/181102 | A1 | 10/2017 |
| WO | WO 2017/184885 | A1 | 10/2017 |
| WO | 2019226755 | A1 | 11/2019 |

OTHER PUBLICATIONS

Tilborg et al., European Journal of Medicinal Chemistry, 2014, 74, p. 411-426. (Year: 2014).*

Gennaro, A.R., ed., Remington's Pharmaceutical Sciences, 17th edition, 1985, Mack Publishing Company, p. 1309-1320. (Year: 1985).*

Definition of prevent, Oxford English Dictionary Online, http://dictionary.oed.com/, accessed online Mar. 27, 2010, especially definition 9a. at p. 2. (Year: 2010).*

International Search Report and Written Opinion issued by the International Searching Authority for Application No. PCT/US2019/033494, dated Jul. 8, 2019, 12 pages.

Bitterman, et al., "Inhibition of Silencing and Accelerated Aging by Nicotinamide, a Putative Negative Regulator of Yeast Sir2 and Human SIRT1," J. Biol. Chem. 277:45099-45107 (2002).

Bogan, et al., "Nicotinic Acid, Nicotinamide and Nicotinamide Riboside: A Molecular Evaluation of NAD+ Precursor Vitamins in Nutritions," Annual Review of Nutrition 28:115-130 (2008).

Bronkowski, et al., "Slowing ageing by design: the rise of NAD+ and sirtuin-activating compounds," Nat. Rev. Mole. Cell. Bio., 17:679-690, (2016).

Frederick, et al., "Loss of NAD Homeostasis Leads to Progressive and Reversible Degeneration of Skeletal Muscle," Cell Metab. 24(2):269-282 (2016).

Guan, et al., "Mechanism of Inhibition of the Human Sirtuin Enzyme SIRT3 by Nicotinamide: Computational and Experimental Studies," PLoS One. 9, e107729 (2014), 18 pages.

Li, et al., "A conserved NAD+ binding pocket that regulates protein-protein interactions during aging," Science 355, 1312-1317, (2017).

MacKay, et al., Niacin: chemical forms, bioavailability, and health effects, Nutr. Rev. 70:357-366 (2012).

(Continued)

*Primary Examiner* — Jonathan S Lau
(74) *Attorney, Agent, or Firm* — Fox Rothschild LLP

(57) ABSTRACT

The present invention relates to amino acid salts of nicotinic acid ribosides and compositions thereof of Formula I, useful in the treatment of disorders and diseases associated with deficiencies in $NAD^+$:

(I)

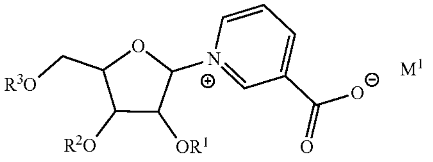

wherein $M^1$, $R^1$, $R^2$, and $R^3$ are as described herein.

18 Claims, No Drawings

(56) References Cited

OTHER PUBLICATIONS

Martens, et al., "Chronic nicotinamide riboside supplementation is well-tolerated and elevates NAD+ in healthy middle-aged and older adults, " Nature Communications 9:1286, pp. 1-11 (2018).
Meldrum, et al., "Aging and the environment affect gamete and embryo potential: can we intervene?" Fertility and Sterility 105: 548-559 (2016).
Mills, K. F., et al., "Long-Term Administration of Nicotinamide Mononucleotide Mitigates Age-Associated Physiological Decline in Mice," Cell Metab. 24(6):795-806 (2016).
Mouchiroud, et al., "The NAD(+)/Sirtuin Pathway Modulates Longevity through Activation of Mitochondrial UPR and FOXO Signaling," Cell 154:430-441, (2014).
Nelson, et al., "The ageing ovary and uterus: new biological insights," Human Reproduction Update 19(1):67-83 (2013).
Qui, et al., "Sirt2-BubR1 acetylation pathway mediates the effects of advanced maternal age on oocyte quality," Aging Cell published by the Anatomical Society and John Wiley & Sons Ltd., 10 pages (2017).
Tatone, et al., Sirtuin Functions in Female Fertility: Possible Role in Oxidative Stress and Aging, Hindawi Publishing Corporation, Oxidative Medicine and Cellular Longevity, vol. 2015, 11 pages (2015).
Tatone, et al., "Sirtuins in gamete biology and reproductive physiology: emerging roles and therapeutic potential in female and male infertility," Human Reproduction Update, pp. 1-23 (2018).
Trammell, et al., "Nicotinamide riboside is uniquely and orally bioavailable in mice and humans", Nat Commun. 7(1):1-14 (2016).
Wilding, "Potential long-term risks associated with maternal aging (the role of the mitochondria)," Fertility and Sterility, 103, 1397-1401 (2015).
Yoshino, J., et al., "Nicotinamide mononucleotide, a key NAD(+) intermediate, treats the pathophysiology of diet- and age-induced diabetes in mice," Cell Metab. 14(4):528-536 (2011).
Zhang, et al., "Sirt2 functions in spindle organization and chromosome alignment in mouse oocyte meiosis," The FASEB Journal 28(3):1435-1445 (2014).
Franchetti et al. (Sep. 20, 2004) "Stereoselective Synthesis of Nicotinamide Beta-Riboside and Nucleoside Analogs", Bioorganic and Medicinal Chemistry Letters, 14(18):4655-4658.
Zhu et al. (Oct. 17, 2012) "A Hydrazine Coupled Cycling Assay Validates the Decrease in Redox Ratio under Starvation in Drosophila", PLoS One, 7(10):e47584 (8 Pages).

* cited by examiner

AMINO ACID SALTS OF NICOTINIC ACID RIBOSIDES AS ANTI-AGING AGENTS

RELATED APPLICATIONS

The application is a U.S. National Phase Application, filed under 35 U.S.C. § 371(c), of International Application No. PCT/US2019/033494, filed May 22, 2019, which claims priority to, and the benefit of, U.S. Provisional Application No. 62/675,065, filed May 22, 2018, the contents of each of which are incorporated herein by reference in their entirety.

FIELD OF THE DISCLOSURE

The present invention relates to inorganic salts of nicotinic acid ribosides and compositions thereof useful in the treatment of disorder and diseases associated with aging.

BACKGROUND OF THE DISCLOSURE

Aging is the result of complex interactions involving biological, physical, and biochemical processes that cause dysfunctions in cells and organs which manifests in a variety of diseases and other outcomes. For example, female fecundity is markedly sensitive to the effects of ageing. For example, the USA Centers for Disease Control has reported that the percentage of assisted reproductive technology (ART) associated pregnancies and births percentages declined steadily among women in their mid-30s onward from approximately 25% of ART cycles resulting in singleton live births to 14% by the age of 40 (Centers for Disease Control and Prevention, American Society for Reproductive Medicine, Society for Assisted Reproductive Technology. 2011 Assisted Reproductive Technology National Summary Report. Atlanta (GA): US Dept of Health and Human Services; 2013). This trend is markedly increased above the age of 40 with the CDC reporting that women older than age 44 have a very low likelihood of success. The percentages of live births and singleton live births declined to about 1% in this group. It is generally considered that a woman's age is the most important factor affecting the chance of a live birth when her own eggs (oocytes) are used.

It is understood that the qualitative deterioration of oocytes due to aging is a fundamental factor in the decline in fertility. In older women, for example, the oocytes are reported to be susceptible to abnormal chromosome division, exhibit decreased mitochondrial quality, low ATP production, increased oxidative stress, and decreased antioxidant levels (Nelson S M, Telfer E E, Anderson R A. The ageing ovary and uterus: new biological insights. Hum Reprod Update. 2013; 19:67-83.; Wilding M. Potential long-term risks associated with maternal aging (the role of the mitochondria). Fertil Steril. 2015; 103:1397-401; 3. Meldrum D R, Casper R F, Diez-Juan A, Simon C, Domar A D, Frydman R. Aging and the environment affect gamete and embryo potential: can we intervene? Fertil Steril. 2016; 105:548-59).

For all of the foregoing reasons, the oocyte represents an excellent target tissue for the evaluation of therapeutic modalities that are expected to have an impact upon the ageing process and, furthermore, offer the prospect of addressing age-related infertility.

One such possible therapeutic modality for treating ageing comprises agents which boost therapeutic levels of $NAD^+$. $NAD^+$ is an essential component of cellular processes necessary to support various metabolic functions. The classic role of $NAD^+$ is a co-enzyme that catalyzes cellular redox reactions, becoming reduced to NADH, in many fundamental metabolic processes, such as glycolysis, fatty acid beta oxidation, or the tricarboxylic acid cycle. In addition to playing these roles, $NAD^+$ has a critical role as the substrate of $NAD^+$-consuming enzymes such as poly-ADP-ribose polymerases (PARPs), sirtuins, and CD38/157 ectoenzymes. These $NAD^+$-consuming enzymes have been known to mediate many fundamental cellular processes.

There are five major precursors and intermediates to synthesize $NAD^+$: tryptophan, nicotinamide, nicotinic acid (NA), nicotinamide riboside (NR), and nicotinamide mononucleotide (NMN). $NAD^+$ can be synthesized de novo by the conversion of the amino acid tryptophan through multiple enzymatic steps to nicotinic acid mononucleotide (NaMN). NaMN is converted to nicotinic acid dinucleotide ($NaAD^+$) by NMN/NaMN adenylyltransferases (NMNATs) and then amidated to $NAD^+$ by $NAD^+$ synthetase.

In mammals, a major pathway of $NAD^+$ biosynthesis is the salvage pathway from nicotinamide. Nicotinamide is converted to NMN, a key NAD+ intermediate, by nicotinamide phosphoribosyltransferase (NAMPT), the rate-limiting enzyme in this pathway. NMNATs then convert NMN into $NAD^+$. NAMPT plays a critical role in regulating cellular NAD+levels. On the other hand, nicotinic acid is converted to NaMN by nicotinic acid phosphoribosyltransferase (NPT). NR needs to be converted to NMN by nicotinamide ribose kinases, NMRK1 and $NMRK^2$ (also known as NRK1 and NRK2), which phosphorylate NR 16. Maintenance of adequate $NAD^+$ biosynthesis is paramount for cell survival and function. Derailment from normal $NAD^+$ homeostasis substantially affects not only the $NAD^+$/NADH pool required for redox reactions but also activities of $NAD^+$-dependent enzymes for crucial cellular functions. It is now becoming a consensus that $NAD^+$ levels decline at cellular, tissue/organ, and organismal levels during the course of aging. Activities of $NAD^+$-consuming enzymes are affected by this $NAD^+$ decline, contributing to a broad range of age-associated.

Nicotinamide adenine dinucleotide is an enzyme cofactor that is essential for the function of several enzymes related to reduction-oxidation reactions and energy metabolism. (Katrina L. Bogan & Charles Brenner, *Nicotinic Acid, Nicotinamide and Nicotinamide Riboside: A Molecular Evaluation of $NAD^+$Precursor Vitamins in Nutritions,* 28, Annual Review of Nutrition 115 (2008). $NAD^+$ functions as an electron carrier in energy metabolism of amino acids, fatty acids and carbohydrates (Bogan & Brenner, 2008). $NAD^+$ is critical for redox reactions and as a substrate for signaling by the PARPs (poly adenoside diphophosphate-ribose polymerases) and the sirtuins (SIRT1 to SIRT7), in the regulation of DNA repair, energy metabolism, cell survival and circadian rhythms (Bronkowski, M. S. & Sinclair, D., *Nat. Rev. Mole. Cell. Bio.,* 17, 679-690, 2016)). Raising $NAD^+$ concentrations delays aging in yeast, files and mice (Mouchiroud et al. *Cell* 154, 464-471, 2014). It has recently also been demonstrated that $NAD^+$ directly regulates protein-protein interactions, the modulation of which may protect against cancer and radiation exposure as well as having a direct impact on aging (Li et al., Science 355, 1312-1317, 2017). Thus increasing bodies of evidence support the idea that interventions using $NAD^+$ intermediates, such as NMN and NR, can bolster the system by restoring the available $NAD^+$ and mitigate physiological decline associated with aging.

Although $NAD^+$ can be synthesized de novo from the amino acid tryptophan, this process does not occur in all tissues, requiring most cells to rely on the salvage pathway (described above) for regenerating $NAD^+$ from other intracellular intermediates, which are primarily made available through dietary sources (Christopher R Martens, et al., *Nat Commun.* 9, 1286, (2018) and Bogan, K. L. & Brenner, C., *Annu. Rev. Nutr.* 28, 115-130, (2008)). Other $NAD^+$ precursors like nicotinic acid and nicotinamide can also be administered to boost NAD cellular bioavailability. However, clinically relevant levels of nicotinic acid are associated with undesirable flushing at therapeutic doses (MacKay, D., Hathcock, J. & Guarneri, E., *Nutr. Rev.* 70, 357-366 (2012)). and nicotinamide does not reliably activate (and may even inhibit) sirtuins despite raising concentrations of NAD (Bitterman, K. J., et al., *J. Biol. Chem.* 277, 45099-45107 (2002); (Gan, X., et al, *PLoS One.* 9, e107729 (2014); and Trammell, S. A. et al. *Nat. Commun.* 7, 12948 (2016)). Therefore, administration of nicotinic acid or nicotinamide is unlikely to be widely adopted for maintaining health and function with aging.

In contrast to nicotinic acid and nicotinamide, administration of $NAD^+$ metabolites such as nicotinamide mononucleotide (NMN) or nicotinamide riboside (NR), appears to increase levels of $NAD^+$ and improves multiple physiological functions in animal models (Yoshino, J. et al., *Cell Metab.* 14, 528-536 (2011): Mills, K. F. et al., *Cell Metab.* 24, 795-806 (2016); and Frederick, D. W. et al., *Cell Metab.* 24, 269-282 (2016)). At least one of these metabolites has been reported to be well tolerated in humans leading to elevation of NAD levels and improved physiological functions albeit that further studies are required to confirm the findings of this exploratory study (Christopher R. Martens, et al., *Nat. Commun.* 9, 1286, (2018)). Furthermore, a recent study showed that single doses of NR stimulated blood cellular $NAD^+$ metabolism in healthy humans in a dose-dependent manner (Trammell, S. A, et al., *Nat. Commun.* 7, 12948 (2016)), showing the limitation of this metabolite. However, many of the known NAD+ metabolites are unstable in a variety of physiological environments and thus do not lend themselves to viable pharmaceutical drugs for administration to patients in need of such metabolites for boosting the NAD+ levels in said patients.

Given the central role that $NAD^+$ plays in critical cellular and physiological pathways, developing novel stable agents with improved properties that can elevate $NAD^+$ levels in disease states and/or during the aging process is necessary to improve the human condition.

SUMMARY OF THE DISCLOSURE

Provided herein are amino acid salts of NaR which salts surprisingly increase cellular $NAD^+$ levels.

A first aspect of the application relates to salts of Formula (I); and enantiomers, stereoisomers, and tautomers thereof,

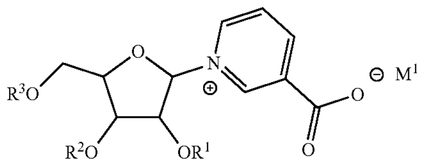

wherein $M^1$ is a zwitterionic amino acid;

$R^1$, $R^2$ and $R^3$ are independently H, $C_1$-$C_6$alkyl, $C_1$-$C_6$haloalkyl, ($C_0$-$C_3$alkylene)C(O)$C_1$-$C_6$alkyl, C(O) $R^a$, —C(O)O$R^a$, —C(O)N$R^aR^b$, or —[$CH_2$—$CH_2$—O]$_k$—$R^a$, or $R^1$ and $R^2$ or $R^2$ and $R^3$, together with the atom to which they are attached, form a 5-membered heterocyclic ring optionally substituted with one or more substituents selected from $C_1$-$C_6$alkyl, $C_2$-$C_6$alkenyl, $C_2$-$C_6$alkynyl, ($C_0$-$C_3$alkylene)$C_3$-$C_8$cycloakyl, ($C_0$-$C_3$alkylene)heterocycloalkyl, ($C_0$-$C_3$alkylene)$C_6$-$C_{14}$aryl, or ($C_0$-$C_3$alkylene)heteroaryl;

$R^a$ and $R^b$ are independently, at each occurrence, H or $C_1$-$C_6$alkyl, wherein the alkyl is optionally substituted with one or more substituents selected from ($C_0$-$C_3$alkylene)$C_3$-$C_8$cycloakyl, ($C_0$-$C_3$alkylene)heterocycloalkyl, ($C_0$-$C_3$alkylene)$C_6$-$C_{14}$aryl, or ($C_0$-$C_3$alkylene)heteroaryl; and k is an integer from 1 to 8.

Another aspect of the present disclosure relates to a pharmaceutical composition comprising a salt of Formula I, or a pharmaceutically acceptable salt thereof, in association with a pharmaceutically acceptable carrier.

Another aspect of the application relates to a method of treating or preventing an age-related disorder comprising administering to a subject in need thereof, an effective amount of a salt of Formula (I), or enantiomer, stereoisomer, or tautomer thereof.

Another aspect of the application relates to a method of treating or preventing infertility comprising administering to a subject in need thereof, an effective amount of a salt of Formula (I), or enantiomer, stereoisomer, or tautomer thereof.

Another aspect of the application relates to a salt of Formula (I), or enantiomer, stereoisomer, or tautomer thereof, for use in a method of treating an age-related disorder.

Another aspect of the application relates to a salt of Formula (I), or enantiomer, stereoisomer, or tautomer thereof, for use in a method of treating infertility.

Another aspect of the application relates to the use of a salt of Formula (I), or enantiomer, stereoisomer, or tautomer thereof, in the manufacture of a medicament for treating an age-related disorder.

Another aspect of the application relates to the use of a salt of Formula (I), or enantiomer, stereoisomer, or tautomer thereof, in the manufacture of a medicament for treating infertility.

Another aspect of the present disclosure relates to a method of improving oocyte quality and maturation, comprising administering to a subject in need thereof, a therapeutically effective amount of a salt of Formula I.

Another aspect of the present disclosure relates to the use of a salt of Formula (I), or enantiomer, stereoisomer, or tautomer thereof, in the manufacture of a medicament for treating an age-related disorder.

In another aspect, the invention comprises treatment of an oocyte with a salt of Formula (I) ex vivo prior to implantation into a subject, for the treatment of age-related infertility.

In another aspect, the invention comprises treatment of a blastocyst with a salt of Formula (I) ex vivo prior to implantation into a subject, for the treatment of age-related infertility.

In another aspect, the invention comprises treatment of an oocyte with a salt of Formula (I) ex vivo prior to implantation into a subject, for the treatment of infertility.

In another aspect, the invention comprises treatment of a blastocyst with a salt of Formula (I) ex vivo prior to implantation into a subject, for the treatment of infertility.

In another aspect, a salt of Formula (I) is provided as a component in solution for use in treating a cell ex vivo for use in the treatment of an age related disorder. In some embodiments, the age related disorder is age-related infertility. In other aspects a salt of Formula (I) is provided as a component in solution for use in treating a cell ex vivo for use in the treatment of infertility.

Another aspect of present disclosure relates to a process for preparing salts of Formula (I), comprising contacting a nicotinic acid mononucleotide derivative of Formula II with a metal-alkali hydroxide under suitable conditions effective to produce the salt of Formula I.

The present disclosure also relates to methods of accelerating recovery from a disease or disorder. The method comprises administering to a subject in need thereof an effective amount of a salt of Formula (I) in combination with the prescribed treatment of said disease.

In another aspect, the present disclosure relates to a cell culture medium for in vitro fertilization comprising: one or more salts of Formula (I) and culturing agents.

DETAILED DESCRIPTION OF THE DISCLOSURE

The present application relates to salts and compositions that are capable of treating or preventing an age-related disorder. The application features methods of treating, preventing or ameliorating a disease or disorder associated with aging by administering to a patient in need thereof a therapeutically effective amount of a salt of Formula (I), or a enantiomer, stereoisomer, or tautomer thereof. The methods of the present application can be used in the treatment of a variety of diseases and disorders by preventing, or ameliorating the process of aging and cellular restoration including, but not limited to, infertility, cellular degradation.

Salts of Formula (I) are potent and are efficacious at clinically achievable doses; are stable in a variety of potential dosage forms; possess acceptable solubility, acceptable pH, are crystalline, have a reduced propensity to absorb water, display ease of handling, —all of which are consistent with the development, manufacture and use of a medicament. In addition, the salts disclosed herein offer increased biological activity toward increased cellular $NAD^+$ levels, increased stability and more physiologically acceptable pH A first aspect of disclosure relates to a salt of Formula I

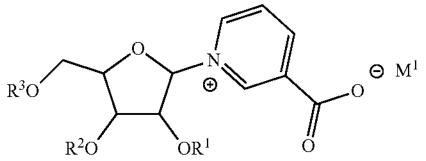

wherein $M^1$, $R^1$, $R^2$, and $R^3$ are as described herein.

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g., an alkyl group) can (but is not required to) be bonded other substituents (e.g., heteroatoms). For instance, an alkyl group that is optionally substituted can be a fully saturated alkyl chain (i.e., a pure hydrocarbon). Alternatively, the same optionally substituted alkyl group can have substituents different from hydrogen For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —$CH_2CN$, —O—($C_1$-$C_6$) alkyl, ($C_1$-$C_6$) alkyl, $C_1$-$C_6$ alkoxy, ($C_1$-$C_6$)haloalkyl, $C_1$-$C_6$ haloalkoxy, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)$(OH)_2$, —OC(O)($C_1$-$C_6$) alkyl, —C(O)($C_1$-$C_6$) alkyl, —OC(O)O($C_1$-$C_6$) alkyl, —$NH_2$, —NH(($C_1$-$C_6$) alkyl), —N(($C_1$-$C_6$) $alkyl)_2$, —NHC(O)($C_1$-$C_6$) alkyl, —C(O)NH($C_1$-$C_6$) alkyl, —$S(O)_2$($C_1$-$C_6$) alkyl, —S(O)NH($C_1$-$C_6$) alkyl, and S(O)N(($C_1$-$C_6$) $alkyl)_2$. The substituents can themselves be optionally substituted. "Optionally substituted" as used herein also refers to substituted or unsubstituted whose meaning is described below.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the term "unsubstituted" means that the specified group bears no substituents.

Unless otherwise specifically defined, the term "aryl" refers to cyclic, aromatic hydrocarbon groups that have 1 to 3 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—($C_1$-$C_6$) alkyl, ($C_1$-$C_6$) alkyl, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)$(OH)_2$, —OC(O)($C_1$-$C_6$) alkyl, —C(O)($C_1$-$C_6$) alkyl, —OC(O)O($C_1$-$C_6$) alkyl, $NH_2$, NH($C_1$-$C_6$) alkyl), N(($C_1$-$C_6$) $alkyl)_2$, —$S(O)_2$—($C_1$-$C_6$) alkyl, —S(O)NH(($C_1$-$C_6$) alkyl, and S(O)N(($C_1$-$C_6$) $alkyl)_2$. The substituents can themselves be optionally substituted. Furthermore when containing two fused rings the aryl groups herein defined may have an unsaturated or partially saturated ring fused with a fully saturated ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic aromatic radical of 5 to 24 ring atoms or a polycyclic aromatic radical, containing one or more ring heteroatoms selected from N, O, or S, the remaining ring atoms being C Heteroaryl as herein defined also means a bicyclic heteroaromatic group wherein the heteroatom is selected from N, O, or S. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiopbene, triazolyl, triazinyl, imidazo[1,2-b]

pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1□$^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo [1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo [1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore when containing two fused rings the aryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

Halogen or "halo" refers to fluorine, chlorine, bromine, or iodine.

Alkyl refers to a straight or branched chain saturated hydrocarbon containing 1-12 carbon atoms. Examples of a ($C_1$-$C_6$) alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" refers to a straight or branched chain saturated hydrocarbon containing 1-12 carbon atoms containing a terminal "O" in the chain, i.e., —O(alkyl). Examples of alkoxy groups include, without limitation, methoxy, ethoxy, propoxy, butoxy, t-butoxy, or pentoxy groups.

"Alkenyl" refers to a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, isobutenyl, pentenyl, or hexenyl. An alkenyl group can be unsubstituted or substituted. Alkenyl, as herein defined, may be straight or branched.

"Alkynyl" refers to a straight or branched chain unsaturated hydrocarbon containing 2-12 carbon atoms. The "alkynyl" group contains at least one triple bond in the chain. Examples of alkenyl groups include ethynyl, propargyl, n-butynyl, iso-butynyl, pentynyl, or hexynyl. An alkynyl group can be unsubstituted or substituted.

The term "alkylene" or "alkylenyl" refers to a divalent alkyl radical. Any of the above mentioned monovalent alkyl groups may be an alkylene by abstraction of a second hydrogen atom from the alkyl. As herein defined, alkylene may also be a $C_1$-$C_6$ alkylene. An alkylene may further be a $C_1$-$C_4$ alkylene. Typical alkylene groups include, but are not limited to, $-CH_2-$, $-CH(CH_3)-$, $-C(CH_3)_2-$, $-CH_2CH_2-$, $-CH_2CH(CH_3)-$, $-CH_2C(CH_3)_2-$, $-CH_2CH_2CH_2-$, $-CH_2CH_2CH_2CH_2-$, and the like.

"Cycloalkyl" means monocyclic or polycyclic saturated carbon rings (e.g., fused, bridged, or spiro rings) containing 3-18 carbon atoms (e.g., $C_3$-$C_{10}$). Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl.

"Heterocyclyl" or "heterocycloalkyl" means monocyclic or polycyclic rings (e.g., fused, bridged, or spiro rings) containing carbon and heteroatoms taken from oxygen, nitrogen, or sulfur and wherein there is not delocalized it electrons (aromaticity) shared among the ring carbon or heteroatoms. The heterocycloalkyl can be a 3-, 4-, 5-, 6-, 7-, 8-, 9- 10-, 11-, or 12-membered ring. The heterocycloalkyl ring structure may be substituted by one or more substituents. The substituents can themselves be optionally substituted. Examples of heterocyclyl rings include, but are not limited to, oxetanyl, azetidinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, and homotropanyl. In accordance with the present application, 3- to 10-membered heterocyclyl refers to saturated or partially saturated non aromatic rings structures containing between 3 and 10 atoms in which there is at least one heteroatoms selected from the group N, O, or S.

The term "hydroxyalkyl" means an alkyl group as defined above, where the alkyl group is substituted with one or more —OH groups. Examples of hydroxyalkyl groups include $HO-CH_2-$, $HO-CH_2-CH_2-$ and $CH_3-CH(OH)-$.

The term "haloalkyl" as used herein refers to an alkyl group, as defined herein, which is substituted one or more halogen. Examples of haloalkyl groups include, but are not limited to, trifluoromethyl, difluoromethyl, pentafluoroethyl, trichloromethyl, etc.

The term "haloalkoxy" as used herein refers to an alkoxy group, as defined herein, which is substituted one or more halogen. Examples of haloalkyl groups include, but are not limited to, trifluoromethoxy, difluoromethoxy, pentafluoroethoxy, trichloromethoxy, etc.

The term "cyano" as used herein means a substituent having a carbon atom joined to a nitrogen atom by a triple bond, i.e., C≡N.

The term "amine" as used herein refers to primary ($R-NH_2$, $R\neq H$), secondary ($R_a-NH$, $R_b\neq H$) and tertiary ($R_a-N$, $R\neq H$) amines. A substituted amine is intended to mean an amine where at least one of the hydrogen atoms has been replaced by the substituent.

The term "amino" as used herein means a substituent containing at least one nitrogen atom. Specifically, $NH_2$, —NH(alkyl) or alkylamino, $-N(alkyl)_2$ or dialkylamino, amide-, carbamide-, urea, and sulfamide substituents are included in the term "amino".

The term "oxo" as used herein refers to an "=O" group.

The term "isomer" refers to salts and/or compounds that have the same composition and molecular weight but differ in physical and/or chemical properties. The structural difference may be in constitution (geometric isomers) or in the ability to rotate the plane of polarized light (stereoisomers). With regard to stereoisomers, the salts of Formula (I) may have one or more asymmetric carbon atom and may occur as racemates, racemic mixtures and as individual enantiomers or diastereomers.

The disclosure also includes pharmaceutical compositions comprising an effective amount of a disclosed salt and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumerate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a salt or pharmaceutical composition is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed salt or a composition to a subject, or administering a prodrug derivative or analog of the salt or composition to the subject, which can form an equivalent amount of active salt within the subject's body.

Salts of the Application

The present application relates to salts or enantiomers, stereoisomers, or tautomers thereof, capable of treating or preventing an age-related disorder, which are useful for the treatment of diseases and disorders associated with aging and cellular restoration.

In some embodiments of the invention, $R^a$ is independently, at each occurrence H, or $C_1$-$C_6$alkyl. In other embodiments, $R^a$ is H. In other embodiments, $R^a$ is $C_1$-$C_6$alkyl. In other embodiments, $R^a$ is $C_1$-$C_6$alkyl substituted with one or more substituents selected from $C_1$-$C_6$alkyl, $C_2$-$C_6$alkenyl, $C_2$-$C_6$alkynyl, ($C_0$-$C_3$alkylene)$C_3$-$C_8$cycloakyl, ($C_0$-$C_3$alkylene)heterocycloalkyl, ($C_0$-$C_3$alkylene)$C_6$-$C_{14}$aryl, or ($C_0$-$C_3$alkylene)heteroaryl. In other embodiments, $R^a$ is $C_1$-$C_6$alkyl substituted with one or more substituents selected from $C_1$-$C_6$alkyl. In other embodiments, $R^a$ is $C_1$-$C_6$alkyl substituted with one or $C_2$-$C_6$alkenyl. In other embodiments, $R^a$ is $C_1$-$C_6$alkyl substituted with one or more $C_2$-$C_6$alkynyl. In other embodiments, $R^a$ is $C_1$-$C_6$alkyl substituted with one or more m ($C_0$-$C_3$alkylene)$C_3$-$C_8$cycloakyl. In other embodiments, $R^a$ is $C_1$-$C_6$alkyl substituted with one or more ($C_0$-$C_3$alkylene) heterocycloalkyl. In other embodiments, $R^a$ is $C_1$-$C_6$alkyl substituted with one or more ($C_0$-$C_3$alkylene)$C_6$-$C_{14}$aryl. In other embodiments, $R^a$ is $C_1$-$C_6$alkyl substituted with one or more ($C_0$-$C_3$alkylene)heteroaryl. In other embodiment $R^a$ is methyl. In other embodiment $R^a$ is methyl substituted with one or more substituents selected from $C_1$-$C_6$alkyl, $C_2$-$C_6$alkenyl, $C_2$-$C_6$alkynyl, ($C_0$-$C_3$alkylene)$C_3$-$C_8$cycloakyl, ($C_0$-$C_3$alkylene)heterocycloalkyl, ($C_0$-$C_3$alkylene)$C_6$-$C_{14}$aryl, or ($C_0$-$C_3$alkylene)heteroaryl.

In a further embodiment, $R^1$ is independently H, $C_1$-$C_6$alkyl, $C_1$-$C_6$haloalkyl, ($C_0$-$C_3$alkylene)C(O)$C_1$-$C_6$alkyl, —C(O)O$R^a$, —C(O)N$R^aR^b$, or —[$CH_2$—$CH_2$—O]$_k$—$R^a$. In another embodiment, $R^1$ is H. In another embodiment, $R^1$ is $C_1$-$C_6$alkyl. In another embodiment, $R^1$ is $C_1$-$C_6$haloalkyl. In another embodiment, $R^1$ is ($C_0$-$C_3$alkylene)C(O)$C_1$-$C_6$alkyl. In another embodiment, $R^1$ is —C(O))O$R^a$. In another embodiment, $R^1$ is —[$CH_2$—$CH_2$—O]$_k$—$R^a$. In another embodiment, $R^1$ is C(O)$C_1$-$C_6$alkyl.

In one embodiment, $R^2$ is independently H, $C_1$-$C_6$alkyl, $C_1$-$C_6$haloalkyl, ($C_0$-$C_3$alkylene)C(O)$C_1$-$C_6$alkyl, —C(O)O$R^a$, —C(O)N$R^aR^b$, or —[$CH_2$—$CH_2$—O]$_k$—$R^a$. In another embodiment, $R^2$ is H. In another embodiment, $R^2$ is $C_1$-$C_6$alkyl. In another embodiment, $R^2$ is $C_1$-$C_6$haloalkyl. In another embodiment, $R^2$ is ($C_0$-$C_3$alkylene)C(O)$C_1$-$C_6$alkyl. In another embodiment, $R^2$ is —C(O)O$R^a$. In another embodiment, $R^2$ is —[$CH_2$—$CH_2$—O]$_k$—$R^a$. In another embodiment, $R^2$ is C(O)$C_1$-$C_6$alkyl.

In one embodiment, $R^3$ is independently H, $C_1$-$C_6$alkyl, $C_1$-$C_6$haloalkyl, ($C_0$-$C_3$alkylene)C(O)$C_1$-$C_6$alkyl, —C(O)O$R^a$, —C(O)N$R^aR^b$, or —[$CH_2$—$CH_2$—O]$_k$—$R^a$. In another embodiment, $R^3$ is H. In another embodiment, $R^3$ is $C_1$-$C_6$alkyl. In another embodiment, $R^3$ is $C_1$-$C_6$haloalkyl. In another embodiment, $R^3$ is ($C_0$-$C_3$alkylene)C(O)$C_1$-$C_6$alkyl. In another embodiment, $R^3$ is —C(O)O$R^a$. In another embodiment, $R^3$ is —[$CH_2$—$CH_2$—O]$_k$—$R^a$. In another embodiment, $R^3$ is C(O)$C_1$-$C_6$alkyl.

In a further embodiment of the salts of the Formula I, $R^1$ and $R^2$, together with the atom to which they are attached, may form a 5-membered heterocyclic ring. In a further embodiment of the salts of the Formula I, $R^1$ and $R^2$, together with the atom to which they are attached, may form a 6-membered heterocyclic ring. In yet a further embodiment of the salts of the Formula I, $R^1$ and $R^2$, together with the atom to which they are attached, may form a 5-membered heterocyclic ring substituted with one or more substituents selected from $C_1$-$C_6$alkyl, $C_2$-$C_6$alkenyl, $C_2$-$C_6$alkynyl, ($C_0$-$C_3$alkylene)$C_3$-$C_8$cycloakyl, ($C_0$-$C_3$alkylene)heterocycloalkyl, ($C_0$-$C_3$alkylene)$C_6$-$C_{14}$aryl, or ($C_0$-$C_3$alkylene)heteroaryl. In yet a further embodiment of the salts of the Formula I, $R^1$ and $R^2$, together with the atom to which they are attached, may form a 6-membered heterocyclic ring substituted with one or more substituents selected from $C_1$-$C_6$alkyl, $C_2$-$C_6$alkenyl, $C_2$-$C_6$alkynyl, ($C_0$-$C_3$alkylene)$C_3$-$C_8$cycloakyl, ($C_0$-$C_3$alkylene)heterocycloalkyl, ($C_0$-$C_3$alkylene)$C_6$-$C_{14}$aryl, or ($C_0$-$C_3$alkylene)heteroaryl.

In a further embodiment of the salts of the Formula I, $R^2$ and $R^3$, together with the atom to which they are attached, may form a 5-membered heterocyclic ring. In a further embodiment of the salts of the Formula I, $R^2$ and $R^3$, together with the atom to which they are attach ed, may form a 6-membered heterocyclic ring. In yet a further embodiment of the salts of the Formula I, $R^2$ and $R^3$, together with the atom to which they are attached, ay form a 5-membered heterocyclic ring substituted with one or more substituents selected from $C_1$-$C_6$alkyl, $C_2$-$C_6$alkenyl, $C_2$-$C_6$alkynyl, ($C_0$-$C_3$alkylene)$C_3$-$C_8$cycloakyl, ($C_0$-$C_3$alkylene)heterocycloalkyl, ($C_0$-$C_3$alkylene)$C_6$-$C_{14}$aryl, or ($C_0$-$C_3$alkylene)heteroaryl. In yet a further embodiment of the salts of the Formula I, $R^2$ and $R^3$, together with the atom to which they are attached, may form a 6-membered heterocyclic ring substituted with one or more substituents selected from $C_1$-$C_6$alkyl, $C_2$-$C_6$alkenyl, $C_2$-$C_6$alkynyl, ($C_0$-$C_3$alkylene) $C_3$-$C_8$cycloakyl, ($C_0$-$C_3$alkylene)heterocycloalkyl, ($C_0$-$C_3$alkylene)$C_6$-$C_{14}$aryl, or ($C_0$-$C_3$alkylene)heteroaryl.

In another embodiment of the salt of Formula I, $M^1$ is a zwitterionic amino acid. In another embodiment, $M^1$ is a zwitterionic amino acid of Formula II:

(II)

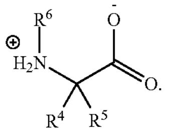

In one embodiment of the salt of Formula I, $R^5$ is H, $C_1$-$C_6$alkyl, $C_2$-$C_6$alkenyl, $C_2$-$C_6$alkynyl, ($C_0$-$C_3$alkylene) $C_3$-$C_8$ cycloakyl, ($C_0$-$C_3$alkylene)heterocycloalkyl, ($C_0$-$C_3$alkylene)$C_6$-$C_{14}$aryl, or ($C_0$-$C_3$alkylene)heteroaryl. In another embodiment, $R^5$ is H. In another embodiment, $R^5$ is $C_1$-$C_6$alkyl. In another embodiment, $R^5$ is $C_2$-$C_6$alkenyl. In another embodiment, $R^5$ is $C_2$-$C_6$alkynyl. In another embodiment, $R^5$ is ($C_0$-$C_3$alkylene)$C_3$-$C_8$cycloakyl. In another embodiment, $R^5$ is ($C_0$-$C_3$alkylene)heterocycloalkyl. In another embodiment, $R^5$ is ($C_0$-$C_3$alkylene)$C_6$-$C_{14}$aryl. In another embodiment, $R^5$ is ($C_0$-$C_3$alkylene) heteroaryl. In another embodiment, $R^5$ is H. $C_1$-$C_4$alkyl substituted with one or more ($C_0$-$C_3$alkylene)$SR^c$.

In another embodiment, $R^5$ is $C_1$-$C_6$alkyl substituted with one or more substituents selected from cyano, halo, SeH, ($C_0$-$C_3$alkylene)$NR^cR^d$, ($C_0$-$C_3$alkylene)$OR^c$, ($C_0$-$C_3$alkylene)OC(O)$R^c$, ($C_0$-$C_3$alkylene)C(O)$OR^c$, ($C_0$-$C_3$alkylene)$SR^c$, ($C_0$-$C_3$alkylene)C(O)$SR^c$, ($C_0$-$C_3$alkylene) SC(O)$R^c$, ($C_0$-$C_3$alkylene)C(O)$NR^cR^d$, ($C_0$-$C_3$alkylene)NC(O)$NR^cR^d$, ($C_0$-$C_3$alkylene)C($NR^c$)$NR^cR^d$, ($C_0$-$C_3$alkylene) $NR^c$C($NR^c$)$NR^cR^d$, ($C_0$-$C_3$alkylene)P(O)$O_nR^cR^d$, ($C_0$-$C_3$alkylene)$S(O)_mNR^cR^d$, ($C_0$-$C_3$alkylene)$S(O)_mOR^c$, or ($C_0$-$C_3$alkylene)$BO_pR^cR^d$. In another embodiment, $R^5$ is $C_2$-$C_6$alkenyl substituted with one or more substituents selected from cyano, halo, SeH, ($C_0$-$C_3$alkylene)$NR^cR^d$, ($C_0$-$C_3$alkylene)$OR^c$, ($C_0$-$C_3$alkylene)OC(O)$R^c$, ($C_0$-$C_3$alkylene)C(O)$OR^c$, ($C_0$-$C_3$alkylene)$SR^c$, ($C_0$-$C_3$alkylene)C(O)$SR^c$, ($C_0$-$C_3$alkylene)SC(O)$R^c$, ($C_0$-$C_3$alkylene)C(O)$NR^cR^d$, ($C_0$-$C_3$alkylene)NC(O)$NR^cR^d$, ($C_0$-$C_3$alkylene)C($NR^c$)$NR^cR^d$, ($C_0$-$C_3$alkylene)$NR^c$C ($NR^c$)$NR^cR^d$, ($C_0$-$C_3$alkylene)P(O)$O_nR^cR^d$, ($C_0$-$C_3$alkylene)$S(O)_mNR^cR^d$, ($C_0$-$C_3$alkylene)$S(O)_mOR^c$, or ($C_0$-$C_3$alkylene)$BO_pR^cR^d$. In another embodiment, $R^5$ is $C_2$-$C_6$ alkynyl substituted with one or more substituents selected from cyano, halo, SeH, ($C_0$-$C_3$alkylene)$NR^cR^d$, $C_0$-$C_3$alkylene)$OR^c$, ($C_0$-$C_3$alkylene)OC(O)$R^c$, ($C_0$-$C_3$alkylene)C(O)O)$R^c$, ($C_0$-$C_3$alkylene)$SR^c$, ($C_0$-$C_3$alkylene)C(O)$SR^c$, ($C_0$-$C_3$alkylene)SC(O)$R^c$, ($C_0$-$C_3$alkylene)C(O)$NR^cR^d$, ($C_0$-$C_3$alkylene)NC(O)$NR^cR^d$, ($C_0$-$C_3$alkylene)C($NR^c$)$NR^cR^d$, ($C_0$-$C_3$alkylene)$NR^c$C ($NR^c$)$NR^cR^d$, ($C_0$-$C_3$alkylene)P(O)$O_nR^cR^d$, ($C_0$-$C_3$alkylene)$S(O)_mNR^cR^d$, ($C_0$-$C_3$alkylene)$S(O)_mOR^c$, or ($C_0$-$C_3$alkylene)$BO_pR^cR^d$. In another embodiment, $R^5$ is ($C_0$-$C_3$alkylene)$C_3$-$C_8$cycloakyl substituted with one or more substituents selected from cyano, halo, SeH, ($C_0$-$C_3$alkylene)$NR^cR^d$, ($C_0$-$C_3$alkylene)$OR^c$, ($C_0$-$C_3$alkylene) OC(O)$R^c$, ($C_0$-$C_3$alkylene)C(O)$OR^c$, ($C_0$-$C_3$alkylene)$SR^c$, ($C_0$-$C_3$alkylene)C(O)$SR^c$, ($C_0$-$C_3$alkylene)SC(O)$R^c$, ($C_0$-$C_3$alkylene)C(O)$NR^cR^d$, ($C_0$-$C_3$alkylene)NC(O)$NR^cR^d$, ($C_0$-$C_3$alkylene)C($NR^c$)$NR^cR^d$, ($C_0$-$C_3$alkylene)$NR^c$C ($NR^c$)$NR^cR^d$, ($C_0$-$C_3$alkylene)P(O)$O_nR^cR^d$, ($C_0$-$C_3$alkylene)$S(O)_m$ $NR^cR^d$, ($C_0$-$C_3$alkylene)$S(O)_mOR^c$, or $C_0$-$C_3$alkylene)$BO_pR^cR^d$. In another embodiment, $R^5$ is ($C_0$-$C_3$alkylene)heterocycloalkyl substituted with one or more substituents selected from cyano, halo, SeH, ($C_0$-$C_3$alkylene)$NR^cR^d$, ($C_0$-$C_3$alkylene)$OR^c$, ($C_0$-$C_3$alkylene) OC(O)$R^c$, ($C_0$-$C_3$alkylene)C(O)$OR^c$, ($C_0$-$C_3$alkylene)$SR^c$, ($C_0$-$C_3$alkylene)C(O)$SR^c$, ($C_0$-$C_3$alkylene)SC(O)$R^c$, ($C_0$-$C_3$alkylene)C(O)$NR^cR^d$, ($C_0$-$C_3$alkylene)NC(O)$NR^cR^d$, ($C_0$-$C_3$alkylene)C($NR^c$)$NR^cR^d$, ($C_0$-$C_3$alkylene)$NR^c$C ($NR^c$)$NR^cR^d$, ($C_0$-$C_3$alkylene)P(O)$O_nR^cR^d$, ($C_0$-$C_3$alkylene)$S(O)_mNR^cR^d$, ($C_0$-$C_3$alkylene)$S(O)_mOR^c$, or ($C_0$-$C_3$alkylene)$BO_pR^cR^d$. In another embodiment, $R^5$ is ($C_0$-$C_3$alkylene)$C_6$-$C_{14}$aryl substituted with one or more substituents selected from cyano, halo, SeH, ($C_0$-$C_3$alkylene)$NR^cR^d$, ($C_0$-$C_3$alkylene)$OR^c$, ($C_0$-$C_3$alkylene) OC(O)$R^c$, ($C_0$-$C_3$alkylene)C(O)$OR^c$, ($C_0$-$C_3$alkylene)$SR^c$, ($C_0$-$C_3$alkylene)C(O)$SR^c$, ($C_0$-$C_3$alkylene)SC(O)$R^c$, ($C_0$-$C_3$alkylene)C(O)$NR^cR^d$, ($C_0$-$C_3$alkylene)NC(O)$NR^cR^d$, ($C_0$-$C_3$alkylene)C($NR^c$)$NR^cR^d$, ($C_0$-$C_3$alkylene)$NR^c$C ($NR^c$)$NR^cR^d$, ($C_0$-$C_3$alkylene)P(O)$O_nR^cR^d$, ($C_0$-$C_3$alkylene)$S(O)_mNR^cR^d$, ($C_0$-$C_3$alkylene)$S(O)_mOR^c$, or ($C_0$-$C_3$alkylene)$BO_pR^cR^d$. In another embodiment, $R^5$ is ($C_0$-$C_3$alkylene)heteroaryl substituted with one or more substituents selected from cyano, halo, SeH, ($C_0$-$C_3$alkylene) $NR^cR^d$, ($C_0$-$C_3$alkylene)$OR^c$, ($C_0$-$C_3$alkylene)OC(O)$R^c$, ($C_0$-$C_3$alkylene)C(O)$OR^c$, ($C_0$-$C_3$alkylene)$SR^c$, ($C_0$-$C_3$alkylene)C(O)$SR^c$, ($C_0$-$C_3$alkylene)SC(O)$R^c$, ($C_0$-$C_3$alkylene)C(O)$NR^cR^d$, ($C_0$-$C_3$alkylene)NC(O)$NR^cR^d$, ($C_0$-$C_3$alkylene)C($NR^c$)$NR^cR^d$, ($C_0$-$C_3$alkylene)$NR^c$C ($NR^c$)$NR^cR^d$, ($C_0$-$C_3$alkylene)P(O)$O_nR^cR^d$, ($C_0$-$C_3$alkylene)$S(O)_mNR^cR^d$, ($C_0$-$C_3$alkylene)$S(O)_mOR^c$, or ($C_0$-$C_3$alkylene)$BO_pR^cR^d$.

In one embodiment of the salt of Formula I, $R^4$ is H, $C_1$-$C_6$alkyl, $C_2$-$C_6$alkenyl, $C_2$-$C_6$alkynyl, ($C_0$-$C_3$alkylene) $C_3$-$C_8$cycloakyl, ($C_0$-$C_3$alkylene)heterocycloalkyl, ($C_0$-$C_3$alkylene)$C_6$-$C_{14}$aryl, or ($C_0$-$C_3$alkylene)heteroaryl. In another embodiment, $R^4$ is H. In another embodiment, $R^4$ is $C_1$-$C_6$alkyl. In another embodiment, $R^4$ is $C_2$-$C_6$alkenyl. In another embodiment, $R^4$ is $C_2$-$C_6$alkynyl. In another embodiment, $R^4$ is ($C_0$-$C_3$alkylene)$C_3$-$C_8$cycloakyl. In another embodiment, $R^4$ is ($C_0$-$C_3$alkylene)heterocycloalkyl. In another embodiment, $R^4$ is ($C_0$-$C_3$alkylene)$C_6$-$C_{14}$aryl. In another embodiment. $R^4$ is ($C_0$-$C_3$alkylene) heteroaryl.

In another embodiment, $R^4$ is $C_1$-$C_6$alkyl substituted with one or more substituents selected from cyano, halo, SeH, ($C_0$-$C_3$alkylene)$NR^cR^d$, ($C_0$-$C_3$alkylene)$OR^c$, ($C_0$-$C_3$alkylene)OC(O)$R^c$, ($C_0$-$C_3$alkylene)C(O)$OR^c$, ($C_0$-$C_3$alkylene)$SR^c$, ($C_0$-$C_3$alkylene)C(O)$SR^c$, ($C_0$-$C_3$alkylene) SC(O)$R^c$, ($C_0$-$C_3$alkylene)C(O)$NR^cR^d$, ($C_0$-$C_3$alkylene)NC (O)$NR^cR^d$, ($C_0$-$C_3$alkylene)C($NR^c$)$NR^cR^d$, ($C_0$-$C_3$alkylene)$NR^c$C($NR^c$)$NR^cR^d$, ($C_0$-$C_3$alkylene)P(O)$O_nR^cR^d$, ($C_0$-$C_3$alkylene)S(O)$_m NR^cR^d$, ($C_0$-$C_3$alkylene)S(O)$_m OR^c$, or ($C_0$-$C_3$alkylene)$BO_pR^cR^d$. In another embodiment, $R^4$ is $C_2$-$C_6$alkenyl substituted with one or more substituents selected from cyano, halo, SeH, ($C_0$-$C_3$alkylene)$NR^cR^d$, ($C_0$-$C_3$alkylene)$OR^c$, ($C_0$-$C_3$alkylene)OC(O)$R^c$, ($C_0$-$C_3$alkylene)C(O)$OR^c$, ($C_0$-$C_3$alkylene)$SR^c$. ($C_0$-$C_3$alkylene)C(O)$SR^c$, ($C_0$-$C_3$alkylene)SC(O)$R^c$, ($C_0$-$C_3$alkylene)C(O)$NR^cR^d$, ($C_0$-$C_3$alkylene)NC(O)$NR^cR^d$, ($C_0$-$C_3$alkylene)C($NR^c$)$NR^cR^d$, ($C_0$-$C_3$alkylene)$NR^c$C($NR^c$)$NR^cR^d$, ($C_0$-$C_3$alkylene)P(O)$O_nR^cR^d$, ($C_0$-$C_3$alkylene)S(O)$_m NR^cR^d$, ($C_0$-$C_3$alkylene)S(O)$_m OR^c$, or ($C_0$-$C_3$alkylene)$BO_pR^cR^d$. In another embodiment, $R^4$ is $C_2$-$C_6$alkynyl substituted with one or more substituents selected from cyano, halo, SeH, ($C_0$-$C_3$alkylene)$NR^cR^d$, ($C_0$-$C_3$alkylene)$OR^c$, ($C_0$-$C_3$alkylene)OC(O(C)$R^c$, ($C_0$-$C_3$alkylene)C((O)$OR^c$, ($C_0$-$C_3$alkylene)$SR^c$, ($C_0$-$C_3$alkylene)C(O)$SR^c$, ($C_0$-$C_3$alkylene)SC(O)$R^c$, ($C_0$-$C_3$alkylene)C(O)$NR^cR^d$, ($C_0$-$C_3$alkylene)NC((O)$NR^cR^d$, ($C_0$-$C_3$alkylene)C($NR^c$)$NR^cR^d$, ($C_0$-$C_3$alkylene)$NR^c$C($NR^c$)$NR^cR^d$, ($C_0$-$C_3$alkylene)P(O)$O_nR^cR^d$, ($C_0$-$C_3$alkylene)S(O)$_m NR^cR^d$, ($C_0$-$C_3$alkylene)S(O)$_m$OC $R^c$, or ($C_0$-$C_3$alkylene)$BO_pR^cR^d$. In another embodiment, $R^4$ is ($C_0$-$C_3$alkylene)$C_3$-$C_8$cycloakyl substituted with one or more substituents selected from cyano, halo, SeH, ($C_0$-$C_3$alkylene)$NR^cR^cR^d$, ($C_0$-$C_3$alkylene)$OR^c$, ($C_0$-$C_3$alkylene)OC(O)$R^c$, ($C_0$-$C_3$alkylene)C(O)$OR^c$, ($C_0$-$C_3$alkylene)$SR^c$, ($C_0$-$C_3$alkylene)C(O)$SR^c$, ($C_0$-$C_3$alkylene)SC(O)$R^c$, ($C_0$-$C_3$alkylene)C(O)$NR^cR^d$, ($C_0$-$C_3$alkylene)NC(O)$NR^cR^d$, ($C_0$-$C_3$alkylene)C($NR^c$)$NR^cR^cR^d$, ($C_0$-$C_3$alkylene)$NR^c$(NR)$NR^cR^d$, ($C_0$-$C_3$alkylene)P(O)$O_nR^cR^d$, ($C_0$-$C_3$alkylene)S(O)$_m NR^cR^d$, ($C_0$-$C_3$alkylene)S(O)$_m$ $OR^c$, or ($C_0$-$C_3$alkylene)$BO_pR^cR^d$. In another embodiment, $R^4$ is ($C_0$-$C_3$alkylene)heterocycloalkyl substituted with one or more substituents selected from cyano, halo, SeH, ($C_0$-$C_3$alkylene)$NR^cR^d$, ($C_0$-$C_3$alkylene)$OR^c$, ($C_0$-$C_3$alkylene)OC(O)$R^c$, ($C_0$-$C_3$alkylene)C(O)$OR^c$, ($C_0$-$C_3$alkylene)$SR^c$, ($C_0$-$C_3$alkylene)C(O)$SR^c$, ($C_0$-$C_3$alkylene)SC(O)$R^c$, ($C_0$-$C_3$alkylene)C(O)$NR^cR^d$, ($C_0$-$C_3$alkylene)NC(O)$NR^cR^d$, ($C_0$-$C_3$alkylene)C($NR^c$)$NR^cR^d$, ($C_0$-$C_3$alkylene)$NR^c$C($NR^c$)$NR^cR^d$, ($C_0$-$C_3$alkylene)P(O)$O_nR^cR^d$, ($C_0$-$C_3$alkylene)S(O)$_m NR^cR^d$, ($C_0$-$C_3$alkylene)S(O)$_m OR^c$, or ($C_0$-$C_3$alkylene)$BO_pR^cR^d$. In another embodiment, $R^4$ is ($C_0$-$C_3$alkylene)$C_6$-$C_{14}$aryl substituted with one or more substituents selected from cyano, halo, SeH, ($C_0$-$C_3$alkylene)$NR^cR^d$, ($C_0$-$C_3$alkylene)$OR^c$, ($C_0$-$C_3$alkylene)OC(O)$R^c$, ($C_0$-$C_3$alkylene)C(O)$OR^c$, ($C_0$-$C_3$alkylene)$SR^c$, ($C_0$-$C_3$alkylene)C(O)$SR^c$, ($C_0$-$C_3$alkylene)SC(O)$R^c$, ($C_0$-$C_3$alkylene)C(O)$NR^cR^d$, ($C_0$-$C_3$alkylene)NC(O)$NR^cR^d$, ($C_0$-$C_3$alkylene)C($NR^c$)$NR^cR^d$, ($C_0$-$C_3$alkylene)$NR^c$C($NR^c$)$NR^cR^d$, ($C_0$-$C_3$alkylene)P(O)$O_nR^cR^d$, ($C_0$-$C_3$alkylene)S(O)$_m NR^cR^d$ ($C_0$-$C_3$alkylene)S(O)$_m OR^c$, or ($C_0$-$C_3$alkylene)$BO_pR^cR^d$. In another embodiment, $R^4$ is ($C_0$-$C_3$alkylene)heteroaryl substituted with one or more substituents selected from cyano, halo, SeH, ($C_0$-$C_3$alkylene)$NR^cR^d$, ($C_0$-$C_3$alkylene)$OR^c$, ($C_0$-$C_3$alkylene)OC(O)$R^c$, ($C_0$-$C_3$alkylene)C(O)$OR^c$, ($C_0$-$C_3$alkylene)$SR^c$, ($C_0$-$C_3$alkylene)C(O)$SR^c$, ($C_0$-$C_3$alkylene)SC(O)$R^c$, ($C_0$-$C_3$alkylene)C(O)$NR^cR^d$, ($C_0$-$C_3$alkylene)NC(O)$NR^cR^d$, ($C_0$-$C_3$alkylene)C($NR^c$)$NR^cR^d$, ($C_0$-$C_3$alkylene)$NR^c$($NR^c$)$NR^cR^d$, ($C_0$-$C_3$alkylene)P(O)$O_nR^cR^d$, ($C_0$-$C_3$alkylene)S(O)$_m$ $NR^cR^d$, ($C_0$-$C_3$alkylene)S(O)$_m OR^c$, or ($C_0$-$C_3$alkylene)$BO_pR^cC^d$.

In another embodiment, $R^6$ is H or $C_1$-$C_6$ alkyl. In another embodiment, $R^6$ is H. In another embodiment, $R^6$ is $C_1$-$C_6$ alkyl. In another embodiment, $R^6$ is $C_1$-$C_6$ alkyl substituted with one or more substituents selected from cyano, halo, ($C_0$-$C_3$alkylene)$NR^cR^d$, or ($C_0$-$C_3$alkylene)$OR^c$. In another embodiment, $R^5$ is H.

Yet in another embodiment, $R^5$ and $R^6$, together with the atoms to which they are attached, my form a 5-membered ring. In another embodiment, $R^5$ and $R^6$, together with the atoms to which they are attached, my form a 5-membered ring substituted with one or more substituents selected from cyano, halo, ($C_0$-$C_3$alkylene)$NR^cR^d$, or ($C_0$-$C_3$alkylene)$OR^c$. In another embodiment, $R^5$ and $R^6$, together with the atoms to which they are attached, my form a 6-membered ring. In another embodiment, $R^5$ and $R^6$, together with the atoms to which they are attached, my form a 6-membered ring substituted with one or more substituents selected from cyano, halo, ($C_0$-$C_3$alkylene)$NR^cR^d$, or ($C_0$-$C_3$alkylene)$OR^c$.

In a further embodiment, $R^d$ is independently, at each occurrence, H or $C_1$-$C_6$alkyl. In another embodiment, $R^d$ is H. In another embodiment, $R^d$ is $C_1$-$C_6$alkyl. In another embodiment, $R^d$ is $C_1$-$C_6$alkyl one or more substituents selected from ($C_0$-$C_3$alkylene)$C_3$-$C_8$cycloakyl, ($C_0$-$C_3$alkylene)heterocycloalkyl, ($C_0$-$C_3$alkylene)$C_6$-$C_{14}$aryl, or ($C_0$-$C_3$alkylene)heteroaryl.

In a further embodiment, $R^c$ is independently, at each occurrence, H or $C_1$-$C_6$alkyl. In another embodiment, $R^c$ is H. In another embodiment, $R^c$ is $C_1$-$C_6$alkyl. In another embodiment, $R^c$ is $C_1$-$C_6$alkyl one or more substituents selected from ($C_0$-$C_3$alkylene)$C_3$-$C_8$cycloakyl, ($C_0$-$C_3$alkylene)heterocycloalkyl, ($C_0$-$C_3$alkylene)$C_6$-$C_{14}$aryl, or ($C_0$-$C_3$alkylene)heteroaryl.

In another embodiment, k at each occurrence is 1, 2, 3, 4, 5, 6, 7, or 8. In another embodiment, k is 1. In another embodiment, k is 2. In another embodiment, k is 3. In another embodiment, k is 4. In another embodiment, k is 5. In another embodiment, k is 6. In another embodiment, k is 7. In another embodiment, k is 8.

In one embodiment, *m* is 0, 1, or 2. In another embodiment, *m* is 0. In another embodiment, *m* is 1. In another embodiment, *m* is 2.

In one embodiment, n is 0, 1, or 2. In another embodiment, n is 0. In another embodiment, n is 1. In another embodiment, n is 2.

In one embodiment, p is 0, 1, or 2. In another embodiment, p is 0. In another embodiment, p is 1. In another embodiment, p is 2.

In some embodiments of the salt of Formula I, the salt has the structure of Formula Ia:

(Ia)

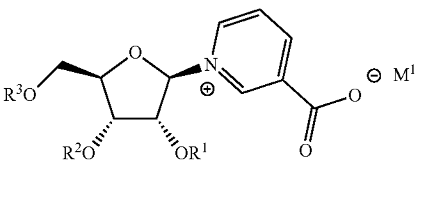

In some embodiments of the salt of Formula I, the salt has the structure of Formula Ib:

(Ib)

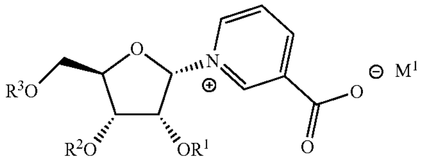

In some embodiments of the salt of Formula I, the salt has the structure of Formula Ic:

(Ic)

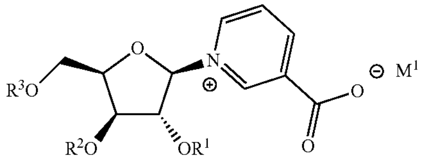

In some embodiments of the salt of Formula I, the salt has the structure of Formula Id:

(Id)

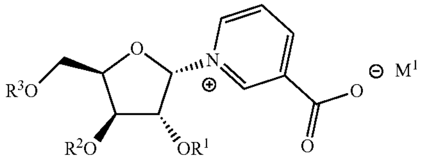

In some embodiments of the salt of Formula I, the salt has the structure of Formula Ie:

(Ie)

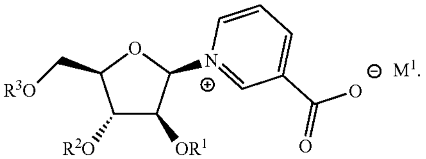

In some embodiments of the salt of Formula I, the salt has the structure of Formula If:

(If)

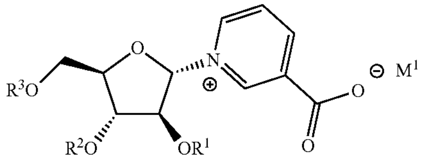

In some embodiments of the salt of Formula I, the salt has the structure of Formula Ig:

(Ig)

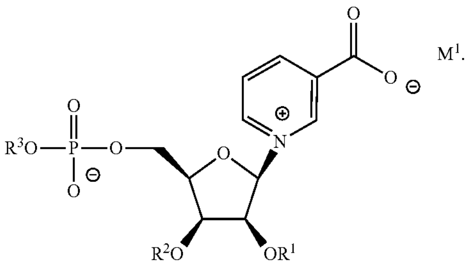

In some embodiments of the salt of Formula I, the salt has the structure of Formula Ih:

(Ih)

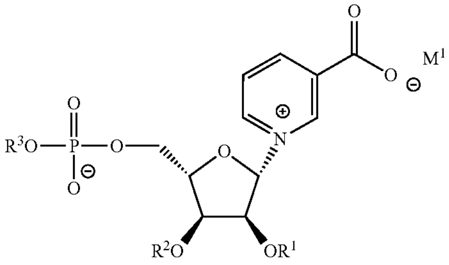

In some embodiments of the salt of Formula I, the salt has the structure of Formula Ii:

(Ii)

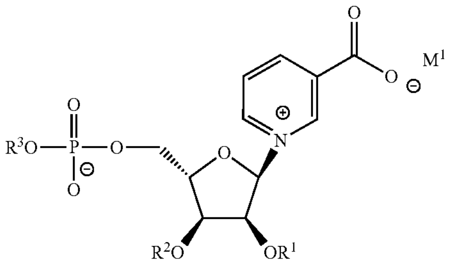

In some embodiments of the salt of Formula I, the salt has the structure of Formula Ij:

(Ij)

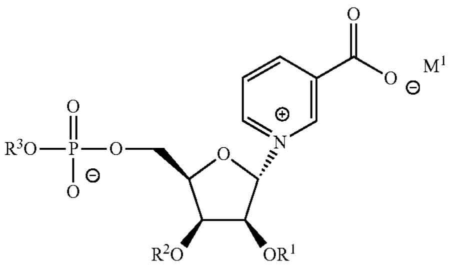

In some embodiments of the salt of Formula I, the salt has the structure of Formula Ik:

(Ik)

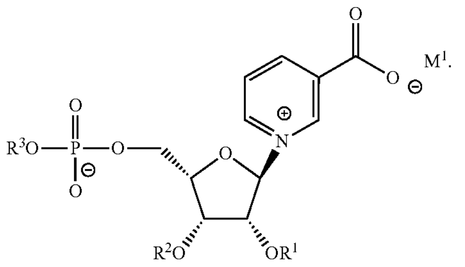

In some embodiments of the salt of Formula I, the salt has the structure of Formula Il:

(Il)

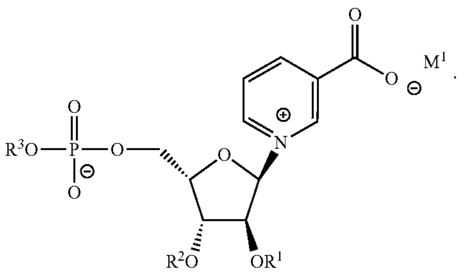

In some embodiments of the salt of Formula I, the salt has the structure of Formula Im:

(Im)

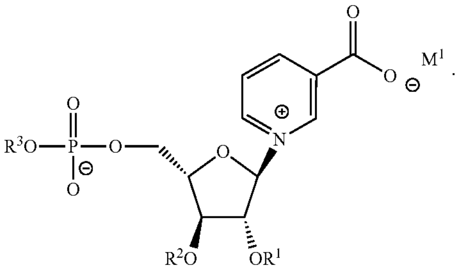

In some embodiments of the salt of Formula I, the salt has the structure of Formula In:

(In)

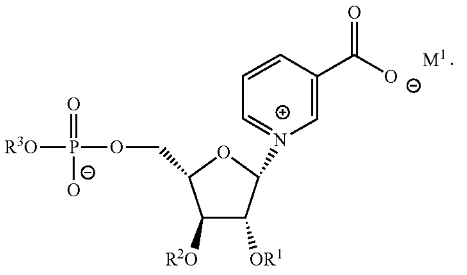

In some embodiments of the salt of Formula I, the salt has the structure of Formula Io:

(Io)

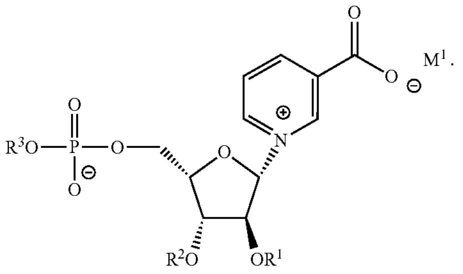

In some embodiments of the salt of Formula I, the salt has the structure of Formula Ir:

(Ir)

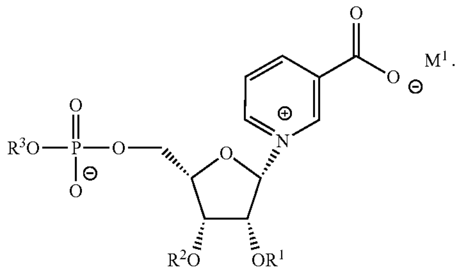

In another embodiment, a suitable salt include without limitation:

(S)-2-Ammonio-3-phenylpropanoate compound with 1-((2R,3R,4S,5R)-3,4-dihydroxy-5-(hydroxymethyl)tetrahydrofuran-2-yl)pyridine-1-ium-3-carboxylate (1:1) (I-001);

(2S,3)-2-Ammonio-3-methylpentanoate compound with 1-((2R,3R,4S,5R)-3,4-dihydroxy-5-(hydroxymethyl)tetrahydrofuran-2-yl)pyridine-1-ium-3-carboxylate (1:1) (I-002);

(S)-2-Ammonio-3-(1H-indol-3-yl)propanoate compound with 1-((2R,3R,4S,5R)-3,4-dihydroxy-5-(hydroxymethyl)tetrahydrofuran-2-yl)pyridine-1-ium-3-carboxylate (1:1) (I-003);

1-((2R,3R,4S,5R)-3,4-dihydroxy-5-(hydroxymethyl)tetrahydrofuran-2-yl)pyridin-1-ium-3-carboxylate-(S)-6-amino-2-ammoniohexanoate (1:1) (I-004);

1-((2R,3R,4S,5R)-3,4-dihydroxy-5-(hydroxymethyl)tetrahydrofuran-2-yl)pyridin-1-ium-3-carboxylate (S)-5-amino-2-ammonio-5-oxopentanoate (1:1) (I-005);

1-((2R,3R,4S,5R)-3,4-dihydroxy-5-(hydroxymethyl)tetrahydrofuran-2-yl)pyridin-1-ium-3-carboxylate-(S)-2-ammonio-4-methylpentanoate (1:1) (I-006);

1-((2R,3R,4S,5R)-3,4-dihydroxy-5-(hydroxymethyl)tetrahydrofuran-2-yl)pyridin-1-ium-3-carboxylate-(S)-2-ammonio-4-carboxybutanoate (1:1) (I-007);

(S)-2-ammonio-3-methylbutanoate-1-((2R,3R,4S,5R)-3,4-dihydroxy-5-(hydroxymethyl)tetrahydrofuran-2-yl)pyridin-1-ium-3-carboxylate (1:1) (I-008);

(S)-2-ammonio-5-guanidinopentanoate-1-((2R,3R,4S,5R)-3,4-dihydroxy-5-(hydroxymethyl)tetrahydrofuran-2-yl) pyridin-1-ium-3-carboxylate (1:1) (I-009); and 1-((2R,3R,4S,5R)-3,4-dihydroxy-5-(hydroxymethyl)tetrahydrofuran-2-yl)pyridin-1-ium-3-carboxylate-(S)-2-ammonio-3-(1H-imidazol-4-yl)propanoate (1:1) (I-010).

Method for Preparation of the Salts

The salts of the present application may be made by a variety of methods, including standard chemistry. Suitable synthetic routes are depicted in the Schemes given below.

The salts of Formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the salt synthesis using methods that are readily apparent to those skilled in the art. The selection processes, as well as the reaction conditions and order of their execution, shall be consistent with the preparation of salts of Formula (I).

Those skilled in the art will recognize if a stereocenter exists in the salts of Formula (I). Accordingly, the present application includes both possible stereoisomers (unless specified in the synthesis) and includes not only racemic salts but the individual enantiomers and/or diastereomers as well. When a compound or salt is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The salts and compounds described herein may be made from commercially available starting materials or synthesized using known organic, inorganic, and/or enzymatic processes.

The salts of the present application can be prepared in a number of ways well known to those skilled in the art of organic synthesis. By way of example, salts of the present application can be synthesized using the methods described below, together with synthetic methods known in the art of synthetic organic chemistry, or variations thereon as appreciated by those skilled in the art. These methods include but are not limited to those methods described below. Salts of the present application can be synthesized by following the steps outlined in General Scheme 1 which comprises different sequences of assembling various intermediates. Starting materials are either commercially available or made by known procedures in the reported literature or as illustrated.

Scheme 1

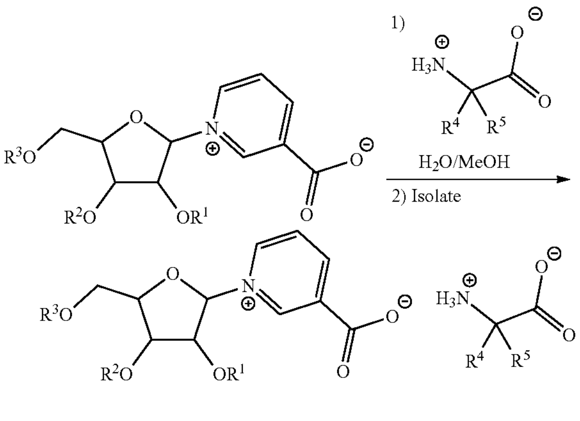

A mixture of enantiomers, diastereomers, cis/trans isomers resulting from the process described above can be separated into their single components by chiral salt technique, chromatography using normal phase, reverse phase or chiral column, depending on the nature of the separation.

It should be understood that in the description and formula shown above, the groups R in the schemes represent $R^3$ as defined above, except where otherwise indicated. Furthermore, for synthetic purposes, the salts of General Scheme 1 are mere representative with elected radicals to illustrate the general synthetic methodology of the salts of Formula (I) as defined herein.

It is also understand that the salts disclosed herein possess a neutral electrical charge and that the structure of Formula I is only representative of genus which, if necessary, may be balanced with counterion to allow the salt to present a neutral electrical charge. Such counterions may include, without limitation, bromine, chlorine, and triflates. In one embodiment, the salt of this invention can be generated in situ without the need to isolated from solution. In some embodiments, the salts disclosed herein can be discrete 1:1 or 1:2 salts. In some embodiments, the salts disclosed herein can also exist in other ratios, e.g., 1:1.5, 1:5, or 1:10.

Methods of Using the Disclosed Salts

Another aspect of the present disclosure relates to a method of treating or preventing a disease or disorder associated with aging, cellular degradation, and/or cellular restoration. Non limiting examples of such diseases and disorders include infertility, age related infertility, age-related loss of eye function, reduction in bone density, obesity and insulin insensitivity. In one embodiment, the salts of Formula (I) are useful in the treatment of age related infertility. In another embodiment the salts of Formula (I) are useful in the treatment of fertility.

Another aspect of the application relates to a method of treating or preventing a disease or disorder associated with aging, cellular degradation, and/or cellular restoration. In one embodiment, the salts of the instant disclosure are useful in the treatment of infertility. In another embodiment The present invention also relates to the use of the salts of Formula I and enantiomers, stereoisomers, and tautomers thereof for the manufacture of medicaments for treating aging, cellular restoration, cellular degradation, or infertility.

Yet another aspect of the present disclosure relates to the method of improving oocyte or blastocyst quality and maturation. The method comprises contacting the oocyte or blastocyst for an effective period of time with IVF media comprising a salt of Formula (I).

In another aspect, the present disclosure provides media containing a salt of Formula (I). The salts of Formula (I) have shown surprising and unexpected prolonged stability in solution and thus are useful in media for exposing eggs, oocytes and/or blastocytes for periods of time necessary for enhancing $NAD^+$ production prior to implantation into a subject suffering from infertility or age-related infertility. In some embodiments, media comprising a salt of Formula (I) is provided. In some embodiments the media comprises the various reagents and factors necessary for the egg, oocyte or blastocyst depending on which stage of maturation and development the egg, oocyte or blastocyst is in. For example, the media can contain any of the agents or factors useful in IVF media listed in Table 1 below:

TABLE 1

| CULTURE MEDIA COMPONENTS |
|---|
| Inorganic salts |
| Energy substrates |
| (glucose, pyruvate and lactate) |
| Essential amino acids |
| (arginine, cysteine, glutamine, histidine, isoleucine, leucine, lysine, methionine, phenylalanine, threonine, tryptophan, tyrosine and valine) |
| Nonessential amino acids |
| (alanine, asparagine, asparatate, glycine, glutamate, proline and serine) |
| Chelators |
| pH indicators |
| Antibiotic agents |
| (such as combination of penicillin and streptomycin) |
| Serum albumin |
| Vitamins |
| Growth factors |
| (insulin or GM-CSF, among others) |

Also provided is a cell culture medium for in vitro fertilization comprising: one or more salts of Formula (I) and culturing agents.

In one embodiment, the culturing agent is an inorganic salt, an energy substrate, an amino acid, a chelator, a pH indicator, an antibiotic, a serum, a vitamin, a growth factor, or any combination thereof. In one embodiment, the inorganic salt is calcium chloride, magnesium chloride, magnesium sulfate, potassium chloride, sodium bicarbonate, sodium chloride, monosodium phosphate, disodium phosphate, or any combination thereof.

In one embodiment, the energy substrate is glucose, pyruvate, lactate, pyruvate, or any combination thereof.

In one embodiment, the amino acid is an essential amino acid. In one embodiment, the essential amino acid is arginine, cysteine, glutamine, glycine, histidine, isoleucine, leucine, lysine, methionine, phenylalanine, proline, threonine, tryptophan, tyrosine, valine, or any combination thereof.

In one embodiment, the amino acid is a non-essential amino acid.

In one embodiment, the non-essential amino acid is alanine, asparagine, aspartate, glutamate, proline, serine, or any combination thereof.

In one embodiment, the chelator is clathro chelate, acetyl acetone, amino polycarboxylic acid, ATMP, BAPTA, BDTH2, citric acid, cryptand, deferasirox, 2,3-dihydrobenzoic acid, 2,3-dimercapto-1-propane sulfonic acid, dimercapto succinic acid, DOTA, DTPMP, EDDHA, EDDS, EDTMP, etidronic acid, fura-2, gluconic acid, homocitric acid, imino diacetic acid, Indo-1, nitrile triacetic acid, pentetic acid (DTPA), phosphonate, phytochelati, poly aspartic acid, sodium poly aspartate, trisodium citrate, transferrin, EDTA, EGTA, or any combination thereof.

In one embodiment, the pH indicator is phenol red, bromothymol blue, alizarin red, 9-aminoacridine, or any combination thereof.

In one embodiment, the antibiotic is actinomycin D, ampicillin, carbenicillin, cefotaxime, fosmidomycin, gentamicin, kanamycin, neomycin, penicillin, polymyxin B, streptomycin, or any combination thereof.

In one embodiment, the serum is human serum albumin, bovine serum albumin, fetal bovine serum, synthetic serum, or any combination thereof.

In one embodiment, the vitamin is ascorbic acid, biotin, menadione sodium bisulfite, mitomycin C, pyridoxamine dihydrochloride, retinyl acetate, (−)-riboflavin, (+)-sodium L-ascorbate, (+)-$\alpha$-tocopherol, vitamin $B_{12}$, thiamine hydrochloride, i-inositol, pyridoxal hydrochloride, nicotinamide, folic acid, D-calcium pantothenate, choline chloride, or any combination thereof.

In one embodiment, the growth factor is adrenomedullin, angiopoietin, bone morphogenetic proteins, macrophage colony-stimulating factor (M-CSF), granulocyte colony-stimulating factor (G-CSF), granulocyte macrophage colony-stimulating factor (GM-CSF), epidermal growth factor, ephrins, erythropoietin, gibroblast growth factor, growth differentiation factor-9, hepatocyte growth factor, insulin, insulin-like growth factors, interleukins, keratinocyte growth factor, migration-stimulating factor, macrophage-stimulating protein, myostatin, neurotrophins, t-cell growth factor, thrombopoietin, transforming growth factor, tumor necrosis factor-alpha, vascular endothelial growth factor, or any combination thereof.

In one embodiment, the cell culture medium further comprises an oocyte, zygote, blastocyst, or any combination thereof Also, provided are kits for IVF media comprising various agents, and factors necessary for oocyte or blastocyst maturation including one or more salts of Formula (I). These agents and cofactors can be dissolved in solution to create the IVF media shortly before use in exposing an oocyte or blastocyst prior to implanting into a patient in need of treatment for infertility or age-related infertility.

The present invention also relates to the use of the salts of Formula I and enantiomers, stereoisomers, and tautomers thereof for the manufacture of medicaments for treating aging, cellular restoration, cellular degradation, or infertility. In certain embodiments the infertility treated is age-related infertility.

Another aspect of the present invention is a pharmaceutical composition comprising the salt of Formula I and a pharmaceutically acceptable carrier.

Another aspect of the present invention is a pharmaceutical composition comprising the salt of Formula I and a pharmaceutically acceptable carrier comprising therapeutically effective amounts of one or more additional therapeutic agents.

In some embodiments, administration of a salt of Formula (I) or a pharmaceutical composition comprising a salt of the present invention and a pharmaceutically acceptable carrier induces a change in the cell cycle or cell viability.

In some embodiments, administration of a salt of Formula (I) or a pharmaceutical composition comprising a salt of the present invention and a pharmaceutically acceptable carrier induces a prophylactic change in the disorder or disease associated with aging.

The disclosed salts of the invention can be administered in effective amounts to treat or prevent a disorder and/or prevent the development of a disorder or disease associated with aging in subjects.

Administration of the disclosed salts can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Effective dosage amounts of the disclosed salts, when used for the indicated effects, range from about 0.5 mg to about 5000 mg of the disclosed salt as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed salt or, in a range of from one amount to another amount in the list of doses. In one embodiment, the compositions are in the form of a tablet that can be scored.

The dosage regimen utilizing the disclosed salt is selected in accordance with a variety of factors including type, species, age, weight, sex and medical condition of the patient; the severity of the condition to be treated; the route of administration; the renal or hepatic function of the patient; and the particular disclosed salt employed. A physician or veterinarian of ordinary skill in the art can readily determine and prescribe the effective amount of the drug required to prevent, counter or arrest the progress of the condition.

Illustrative pharmaceutical compositions are tablets and gelatin capsules comprising a salt of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the salt such as cyclodextrin, hydroxypropyl-cyclodextrin, PEG400, PEG200.

Most of the amino acids can possess buffering properties as the salts, and their multiple pKa values can result in a greater range of stable pH values that is more compatible with biological fluids and, consequently, more suitable for IV administration. Naturally occurring amino acids, NMN, and NaMN are endogenous substances. Mixtures of such are therefore unlikely to be toxic to mammals. Some of the products may have enhanced solubility and solid form stabilities. In one embodiment, the salt may have enhanced aqueous solubility. In one embodiment, the salt may have enhanced solid form stability. In one embodiment, the salt may have enhanced chemical stability.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

The following salts disclosed herein were prepared using the general synthetic methodology including without limitation reagents such as valine, leucine, alanine, isoleucine, methionine, phenylalanine, tryptophane, and tyrosine. Suitable solvents such as methanol, ethanol, water, acetic acid. ethylene glycol, isopropanol were also used.

Abbreviations Used in the Following Examples and Elsewhere Herein are

AcOH acetic acid
anh. anhydrous
atm atmosphere
aq. aqueous
br broad
Boc tert-butyloxycarbonyl
brine saturated aqueous sodium chloride
n-BuLi n-butyllithium
n-BuOH n-butanol
Calc'd calculated
$CDCl_3$ deuterated chloroform
CDI carbonyldiimidazole
Chloroform-d deuterated chloroform
d doublet
dd doublet of doublets
dt doublet of triplets
$D_2O$ deuterated water (deuterium oxide)
DCE dichloroethane
DCM dichloromethane
DIAD diisopropyl azodicarboxylate
DIPEA N,N-diisopropylethylamirne
DMAc N,N-dimethyl acetamide
DMAP N,N-dimethylpyridin-4-amine
DME 1,2-dimethoxyethane
DMEDA N,N'-dimethylethylenediamine
DMF N,N,-dimethyl formamide
DMSO dimethyl sulfoxide
DMSO-$d_6$ deuterated dimethyl sulfoxide
EDA ethylenediamine
EDC 1-ethyl-3-(3-dimethylaminopropyl)carbodiimide
$Et_2O$ diethyl ether
EtOAc ethyl acetate
EtOH ethanol
ESI electrospray ionization
g gram
h hour(s)
H hydrogen
$^1H$ NMR nuclear magnetic resonance (proton nucleus)
HATU [bis(dimethylamino)methylene]-1H-1,2,3-triazolo[4,5-b]pyridinium 3-oxide hexafluorophosphate
HBTU 3-[bis(dimethylamino)methylene]-3H-benzotriazol-1-oxide hexafluorophosphate
HOBt hydroxybenzotriazole
HPLC high pressure (or performance) liquid chromatography
Hz hertz
J coupling constant
$KHCO_3$ potassium bicarbonate KHMDS potassium hexamethyldisilazide
KOAc potassium acetate
LCMS liquid chromatography mass spectrometry
LHMDS lithium hexamethyldisilazide
[#]M molar concentration
*m* multiplet
$[M+H]^+$ molecular ion plus hydrogen
$[M-tBu+H]^+$ molecular ion minus tert-butyl plus hydrogen
mCPBA meta-chloroperoxybenzoic acid
$Me_2NH$ dimethylamine
$Me_4NBr$ tetramethylammonium bromide
MeCN acetonitrile
$MeNH_2$ methylamine
MeOH methanol
Methanol-$d_4$ deuterated methanol
2-MeTHF 2-methyl tetrahydrofuran
mg milligram
MHz megahertz
min min
mmol millimole
mL milliliter
MS mass spectrometry
MS ES mass spectrometry electrospray
$Ms_2O$ methanesulfonic anhydride
MTBE methyl tert-butyl ether
MW microwave
m/z mass-to-charge ratio
μL microliter
$N_2$ nitrogen
$NaHCO_3$ sodium bicarbonate
NaMN nicotinic acid mononucleotide
NIS N-iodosuccinimide
NMP N-methyl-2-pyrrolidone
NMR nuclear magnetic resonance
PEPPSI-iPr [1,3-bis(2,6-diisopropylphenyl)imidazol-2-ylidene](3-chloropyridyl)palladium(II) dichloride
$PdCl_2$(Amphos) bis(di-tert-butyl(4-dimethylaninophenyl)phosphine) dichloropalladium(II)
$Pd_2(dba)_3$ tris(dibenzylideneacetone)dipalladium(0)
$Pd(OAC)_2$ palladium(II) acetate
$PdCl_2$(dppf) [1,1'-bis(diphenylphosphino)ferrocene]dichloropalladium(II)
$PdCl_2(MeCN)_2$ bis(acetonitrile)dichloropalladium(II)
$PdCl_2(PPh_3)_2$ bis(triphenylphosphinepalladium(II) dichloride
$Pd(P(Cy)_3)_2Cl_2$ dichlorobis(tricyclohexylphosphine)palladium(II)
$Pd(PPh_3)_4$ tetrakis(triphenylphosphine)palladium(0)
$Pd(t-Bu_3P)_2$ bis(tri-tert-butylphosphine)palladium(0)
pH potential of hydrogen
PMB 4-methoxybenzyl
PMBCl 4-methoxybenzyl chloride
ppm parts per million
prep preparative
py pyridine
q quartet
qd quartet of doublets
quant. quantitative
quin. quintuplet
quind quintuplet of doublets
RBF round-bottom flask
Rt retention time
rt room temperature
s singlet
sat. saturated
sat. aq. saturated aqueous SEMCl 2-(trimethylsilyl)ethoxymethyl chloride
t triplet
t-BuLi tert-butyllithium
td triplet of doublets
TMS trimethylsilyl
TMSCl trimethylsilyl chloride
tt triplet of triplets
T3P polyphosphonic anhydride
TBAB tetrabutylammonium bromide
TEA triethylamine
TFA trifluoroacetic acid
TFAA trifluoroacetic anhydride
THF tetrahydrofuran
TLC thin layer chromatography
TPPO triphenylphosphine oxide
XantPhos 4,5-bis(diphenylphosphino)-9,9-dimethylxanthene
XPhos 2-dicyclohexylphosphino-2',4',6'-triisopropylbiphenyl Example 1. Synthesis of (S)-2-Ammonio-3-phenylpropanoate compound with 1-((2R,3R,4S,5R)-3,4-dihydroxy-5-(hydroxymethyl)tetrahydrofuran-2-yl)pyridine-1-ium-3-carboxylate (1:1)

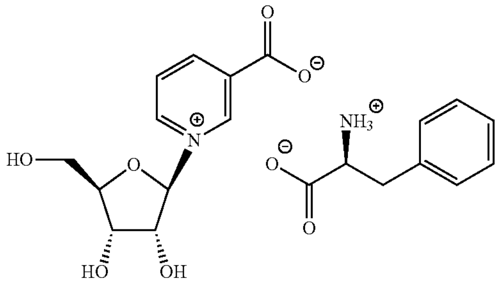 [SMILES: O=C([O-])c1ccc[n+]([C@@H]2O[C@H](CO)[C@@H](O)[C@H]2O)c1 ; [NH3+][C@@H](Cc1ccccc1)C(=O)[O-]]

A 50 mL 1 N RBF fitted with a water condenser was charged with NaR (0.100 g, 0.392 mmol, 1 eq) and 10 ml of distilled deionised water and mixed to form a solution, a faint suspension is also ok. This solution was cooled using an ice/water bath. To this solution was then added L-phenylalanine in one portion (0.0647 g, 392 mmol, 1.0 eq). After this addition the pH was ~4.9-5.2 and all solids had gone into solution. The flask was then removed and the colourless solution frozen using liquid nitrogen. While the flask was frozen it was connected to the freeze dryer. This will slowly remove water. Once dried the product is rendered as a colourless solid.

Yield: 160.6 mg (98%)

Melting point: 130-133° C. (Corrected, degradation), 145° C. outgassing

Analytical data. $^1H$-NMR (400 MHz, $D_2O$) δ=9.47 (s, 1H), 9.18 (d, 1H), 8.96 (d, 1H), 8.21 (dd, 1H), 7.48-7.32 (m, 5H), 6.25 (d, 1H), 4.51 (m, 2H), 4.38 (t, 1H), 4.10-4.00 (2×dd, 2H), 3.92 (dd, 1H), 3.31 (dd, 1H), 3.15 (dd, 1H) ppm Example 2. Synthesis of (2S,3S)-2-Ammonio-3-methylpentanoate compound with 1-((2R,3R,4S,5R)-3,4-dihydroxy-5-(hydroxymethyl)tetrahydrofuran-2-yl)pyridine-1-ium-3-carboxylate (1:1)

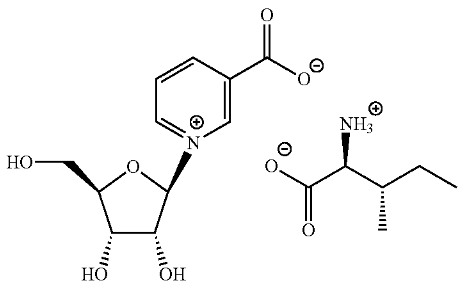

A 50 mL 1 N RBF fitted with a water condenser was charged with NaR (0.100 g, 0.392 mmol, 1 eq) and 20 ml of distilled deionised water and mixed to form a solution, a faint suspension is also ok. This solution was cooled using an ice/water bath. To this solution was then added L-isoleucine in one portion (0.080 g, 392 mmol, 1.0 eq). After this addition the pH was ~4.6-4.9 and all solids had gone into solution.

The flask was then removed and the colourless solution frozen using liquid nitrogen. While the flask was frozen it was connected to the freeze dryer. This will slowly remove water. Once dried the product is rendered as a colourless solid.

Yield: 147.1 mg (97%)

Melting point: 144-148° C. (Corrected, degradation)

Analytical data. $^1$H-NMR (400 MHz, $D_2O$) δ=9.48 (s, 1H), 9.18 (d, 1H), 8.98 (d, 1H), 8.21 (dd, 1H), 6.24 (d, 1H), 4.48-4.55 (m, 2H), 4.38 (t, 1H), 4.07 (dd, 1H), 3.93 (dd, 1H), 3.69 (d, 1H), 2.00 (m, 1H), 1.55-1.45 (m, 1H), 1.35-1.24 (m, 1H), 1.04 (d, 3H), 0.95 (t, 3H) ppm Example 3. Synthesis of (S)-2-Ammonio-3-(1H-indol-3-yl)propanoate compound with 1-((2R,3R,4S,5R)-3,4-dihydroxy-5-(hydroxymethyl)tetrahydrofuran-2-yl)pyridine-1-ium-3-carboxylate (1:1)

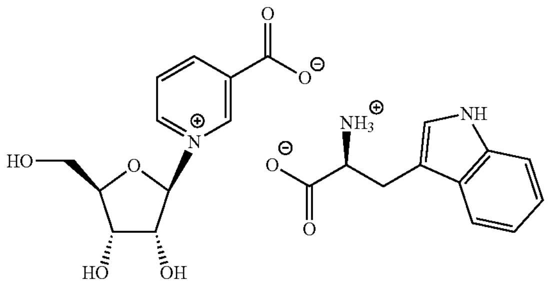 [SMILES: O=C([O-])c1ccc[n+]([C@@H]2O[C@H](CO)[C@@H](O)[C@H]2O)c1 ; [NH3+][C@@H](Cc1c[nH]c2ccccc12)C(=O)[O-]]

A 50 mL 1 N RBF fitted with a water condenser was charged with NaR (0.100 g, 0.392 mmol, 1 eq) and 30 ml of distilled deionised water and mixed to form a solution, a faint suspension is also ok. This solution was cooled using an ice/water bath. To this solution was then added L-tryptophan in one portion (0.080 g, 392 mmol, 1.0 eq). After this addition the pH was ~4.9-5.2 and all solids had gone into solution.

The flask was then removed and the colourless solution frozen using liquid nitrogen. While the flask was frozen it was connected to the freeze dryer. This will slowly remove water. Once dried the product is rendered as a yellow solid.

Yield: 171.8 mg (96%)

Melting point: 117-126° C. (Corrected, degradation), 133° C. outgassing

Analytical data. $^1$H-NMR (400 MHz, $D_2O$) δ=9.42 (s, 1H), 9.12 (d, 1H), 8.93 (d, 1H), 8.15 (dd, 1H), 7.72 (d, 1H), 7.53 (d, 1H), 7.30 (s+t, 2H), 7.20 (t, 1H), 6.28 (d, 1H), 4.481 (m, 2H), 4.38 (t, 1H), 4.10-4.00 (m, 2H), 3.92 (dd, 1H), 3.51 (dd, 1H), 3.32 (dd, 1H) ppm Example 4. Synthesis of 1-((2R,3R,4S,5R)-3,4-dihydroxy-5-(hydroxymethyl)tetrahydrofuran-2-yl)pyridin-1-ium-3-carboxylate-(S)-6-amino-2-ammoniohexanoate (1:1)

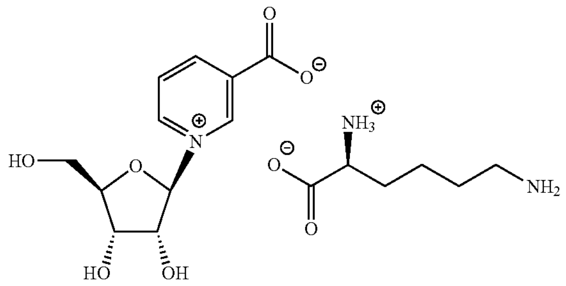 [SMILES: O=C([O-])c1ccc[n+]([C@@H]2O[C@H](CO)[C@@H](O)[C@H]2O)c1 ; NCCCC[C@H]([NH3+])C(=O)[O-]]

A 250 mL 1 N RBF fitted with a water condenser was charged with NaR (0.200 g, 0.784 mmol, 1 eq) and 40 ml of distilled deionised water and mixed to form a solution, a faint suspension is also ok. This solution was cooled using an ice/water bath. To this solution was then added L-lysine in one portion (0.115 g, 0.744 mmol, 0.95 eq). After this addition the pH was 9.63 and all solids had gone into solution.

The flask was then removed and the colourless solution frozen using liquid nitrogen. While the flask was frozen it was connected to the freeze dryer. This will slowly remove water. Once dried the product is rendered as a yellow to brown coloured solid.

Yield: Quantitative

Analytical data. $^1$H-NMR (400 MHz, $D_2O$) δ=9.43 (s, 1H), 9.13 (d, 1H), 8.92 (d, 1H), 8.17 (dd, 1H), 6.21 (d, 1H), 4.48 (m, 2H), 4.33 (t, 1H), 4.02 (dd, 1K), 3.88 (dd, 1H), 3.46 (t, 1H), 2.98 (d, 2H), 1.8-1.6 (m, 4H), 1.5-1.3 (m, 2H) ppm Example 5. Synthesis of 1-((2R,3R,4S,5R)-3,4-dihydroxy-5-(hydroxymethyl)tetrahydrofuran-2-yl)pyridin-1-ium-3-carboxylate (S)-5-amino-2-ammonio-5-oxopentanoate (1:1)

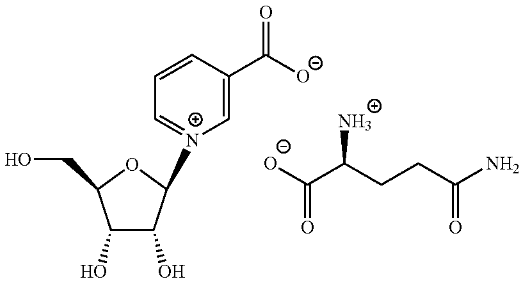 [SMILES: O=C([O-])c1ccc[n+]([C@@H]2O[C@H](CO)[C@@H](O)[C@H]2O)c1 ; NC(=O)CC[C@H]([NH3+])C(=O)[O-]]

A 100 mL 1 N RBF fitted with a water condenser was charged with NaR (0.200 g, 0.784 mmol, 1 eq) and 15 ml of distilled deionised water and mixed to form a solution, a faint suspension is also ok. This solution was cooled using an ice/water bath. To this solution was then added L-glutamine in one portion (0.109 g, 0.744 mmol, 0.95 eq). After this addition the pH was 4.95 and all solids had gone into solution.

The flask was then removed and the colourless solution frozen using liquid nitrogen. While the flask was frozen it was connected to the freeze dryer. This will slowly remove water. Once dried the product is rendered as a yellow to brown coloured solid.

Yield: Quantitative

Analytical data. $^1$H-NMR (400 MHz, $D_2O$) δ=9.45 (s, 1H), 9.13 (d, 1H), 8.92 (d, 1H), 8.17 (dd, 1H), 6.20 (d, 1H), 4.50-4.43 (m, 2H), 4.33 (t, 1H), 4.03 (dd, 1H), 3.89 (dd, 1H), 3.75 (t, 1H), 2.50-2.37 (ddd, 2H), 2.15-2.07 (m, 2H) ppm Example 6. 1-((2R,3R,4S,5R)-3,4-dihydroxy-5-(hydroxymethyl)tetrahydrofuran-2-yl)pyridin-1-ium-3-carboxylate-(S)-2-ammonio-4-methylpentanoate (1:1)

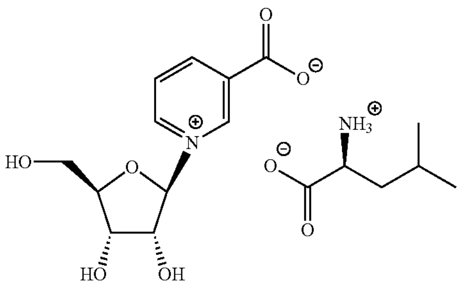

A 100 mL 1 N RBF fitted with a water condenser was charged with NaR (0.200 g, 0.784 mmol, 1 eq) and 15 ml of distilled deionised water and mixed to form a solution, a faint suspension is also ok. This solution was cooled using an ice/water bath. To this solution was then added L-leucine in one portion (0.098 g, 0.744 mmol, 0.95 eq). After this addition the pH was 5.61 and all solids had gone into solution.

The flask was then removed and the colourless solution frozen using liquid nitrogen. While the flask was frozen it was connected to the freeze dryer. This will slowly remove water. Once dried the product is rendered as a colourless.

Yield: Quantitative

Analytical data. $^1$H-NMR (400 MHz, $D_2O$) δ=9.43 (s, 1H), 9.12 (d, 1H), 8.92 (d, 1H), 8.17 (dd, 1H), 6.21 (d, 1H), 4.50-4.43 (m, 2H), 4.34 (t, 1H), 4.03 (dd, 1H), 3.89 (dd, 11H), 3.71 (app t, 1H), 1.8-1.6 (m, 3H), 0.98-0.9 (2×d, 6H) ppm Example 7. Synthesis of 1-((2R,3R,4S,5R)-3,4-dihydroxy-5-(hydroxymethyl)tetrahydrofuran-2-yl)pyridin-1-ium-3-carboxylate-(S)-2-ammonio-4-carboxybutanoate (1:1)

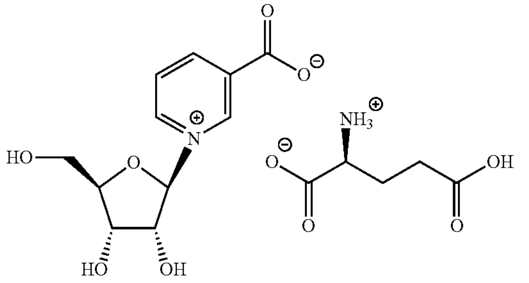 [SMILES: O=C([O-])c1ccc[n+]([C@@H]2O[C@H](CO)[C@@H](O)[C@H]2O)c1 ; [NH3+][C@@H](CCC(=O)O)C(=O)[O-]]

A 100 mL 1 N RBF fitted with a water condenser was charged with NaR (0.200 g, 0.784 mmol, 1 eq) and 15 ml of distilled deionised water and mixed to form a solution, a faint suspension is also ok. This solution was cooled using an ice/water bath. To this solution was then added L-glutamic acid in one portion (0.110 g, 0.744 mmol, 0.95 eq). After this addition the pH was 3.52 and all solids had gone into solution.

The flask was then removed and the colourless solution frozen using liquid nitrogen. While the flask was frozen it was connected to the freeze dryer. This will slowly remove water. Once dried the product is rendered as a colourless.

Yield: Quantitative

Analytical data. $^1$H-NMR (400 MHz, $D_2O$) δ=9.45 (app m, 1H), 9.15 (app m, 1H), 8.94 (app m, 1H), 8.18 (app m, 1H), 6.21 (app m, 1H), 4.50-4.43 (m, 2H), 4.34 (m, 1H), 4.05 (m, 1H), 3.89 (m, 1H), 3.78 (app m, 1H), 2.55 (m, 2H), 2.25-2.15 (m, 2H) ppm Example 8. Synthesis of (S)-2-ammonio-3-methylbutanoate-1-((2R,3R,4S,5R)-3,4-dihydroxy-5-(hydroxymethyl)tetrahydrofuran-2-yl)pyridin-1-ium-3-carboxylate (1:1)

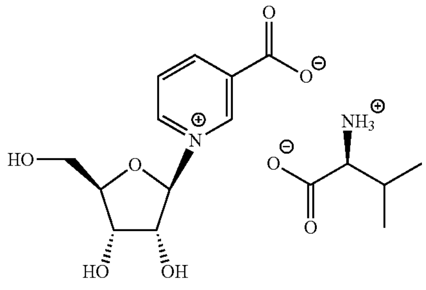

A 100 mL 1 N RBF fitted with a water condenser was charged with NaR (0.200 g, 0.784 mmol, 1 eq) and 15 ml of distilled deionised water and mixed to form a solution, a faint suspension is also ok. This solution was cooled using an ice/water bath. To this solution was then added L-valine in one portion (0.087 g, 0.744 mmol, 0.95 eq). After this addition the pH was 5.67 and all solids had gone into solution.

The flask was then removed and the colourless solution frozen using liquid nitrogen. While the flask was frozen it was connected to the freeze dryer. This will slowly remove water. Once dried the product is rendered as a colourless.

Yield: Quantitative

Analytical data. $^1$H-NMR (400 MHz, $D_2O$) δ=9.43 (s, 1H), 9.13 (d, 1H), 8.92 (dt, 1H), 8.17 (dd, 1H), 6.21 (d, 1H), 4.50-4.43 (m, 2H), 4.34 (t, 1H), 4.03 (dd, 1H), 3.89 (dd, 1H), 3.59 (d, 1H), 2.30-2.20 (m, 1H), 1.03, 0.97 (2×d, 6H) ppm Example 9. Synthesis of (S)-2-ammonio-5-guanidinopentanoate-1-((2R,3R,4S,5R)-3,4-dihydroxy-5-(hydroxymethyl)tetrahydrofuran-2-yl)pyridin-1-ium-3-carboxylate (1:1)

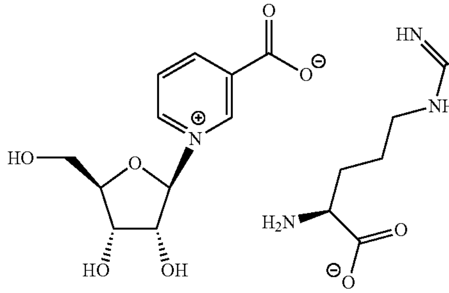

A 100 mL 3N RBF was charged with NaR (0.25 g, 0.979 mmol, 1 eq) and 25 ml of distilled deionised water and mixed to form a solution, a faint suspension is also ok. This solution was cooled using an ice/water bath. To this solution was then added L-Arginine in one portion (0.152, 0.979 mmol, 1.0 eq).

The flask was then removed and the colourless solution frozen using liquid nitrogen. While the flask was frozen it was connected to the freeze dryer. This will slowly remove water. Once dried the product is rendered as a yellow solid.

Yield: Quantitative

Analytical data. $^1$H-NMR (400 MHz, $D_2O$) δ=9.42 (s, 1H), 9.12 (d, 1H), 8.93 (d, 1H), 8.15 (dd, 1H), 6.28 (d, 1H), 4.481 (m, 2H), 4.38 (t, 1H), 4.10-3.9 (dq, 2H), 3.3 (m, 1H), 3.18 (dd, 1H). 1.5-1.8 (m, 4H) ppm Example 10. Synthesis of 1-((2R,3R,4S,5R)-3,4-dihydroxy-5-(hydroxymethyl)tetrahydrofuran-2-yl) pyridin-1-ium-3-carboxylate-(S)-2-ammonio-3-(1H-imidazol-4-yl)propanoate (1:1)

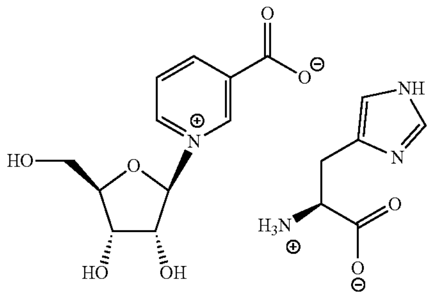 [SMILES: O=C([O-])c1ccc[n+]([C@@H]2O[C@H](CO)[C@@H](O)[C@H]2O)c1 ; [NH3+][C@@H](Cc1c[nH]cn1)C(=O)[O-]]

A 100 mL 3N RBF was charged with NaR (0.25 g, 0.979 mmol, 1 eq) and 25 ml of distilled deionised water and mixed to form a solution, a faint suspension is also ok. This solution was cooled using an ice/water bath. To this solution was then added L-Histidine in one portion (0.152 g, 0.979 mmol, 1.0 eq).

The flask was then removed and the colourless solution frozen using liquid nitrogen. While the flask was frozen it was connected to the freeze dryer. This will slowly remove water. Once dried the product is rendered as a colourless solid.

Yield: Quantitative.

Analytical data. $^1$H-NMR (400 MHz, $D_2O$) δ=9.42 (s, 1H), 9.12 (d, 1H), 8.93 (d, 1H), 8.15 (dd, 1H), 7.72 (d, 1H), 7.05 (s, 1H), 6.28 (d, 1H), 4.481 (m, 2H), 4.38 (t, 1H), 4.10-3.9 (dt, 2H), 4.0 (q, 4H), 3.18 (dd, 2H) ppm.

Example 11. NAD Cell Assays

NAD levels were assayed based on the NAD cycling method of Zhu and Rand, *PLoS One* (2012), herein incorporated by reference. COV434 cells were maintained in 6 well plates and treated with the indicated compounds at a concentration of 200 uM for 4 hr. Media was removed, plates were washed in cold PBS and cells were scraped down in NAD extraction buffer containing 10 mM nicotinamide, 50 mM Tris HCl, 0.1% Triton X-100. Cells were homogenised by sonication for 5 seconds, and samples were centrifuged at 7,000 g for 5 min at 4 degrees. Aliquots were taken for later protein assay, and samples were then passed through 10 kDa amicon filters at 14,000 g, 30 min at 4 degrees to remove proteins from the sample. Each sample was measured in technical triplicate, with 25 μL sample added to 100 μL ADH cycling mix (0.2 mg/ml alcohol dehydrogenase enzyme, 2% ethanol, 100 mM Tris pH 8.5). Samples were allowed to cycle for 10 min at room temperature, followed by 50 μL addition of an MTT/PMS solution (0.1 mM phenazine methosulfate, 0.8 mM 3(4,5-Dimethylthiazol-2-yl)-2,5-diphenyltetrazolium bromide), 100 mM Tris-HCl pH 8.5). Plates were then incubated for 15 min and absorbance was measured at 570 nM. NAD concentrations were extrapolated from a standard curve, and normalised to protein concentrations determined by BCA protein assay.

The results of the assay described above are shown in Table 2 (below). The adjusted fold increase is obtained through a direct comparison on a mole per mole basis between the compared salt and its parent counterpart. In other words, the instant compounds derived from NaR parent molecule will only have their NAD activity level measured against NaR based on the same amount (mole) of salt tested in the cell. For example, the fold increase of compound I-002 is based on the NAD activity observed in a direct comparison for the same amount of mole in the cell and that of the NaR parent. Similarly, the fold increase of i-003 is based on the direct comparison with NaR.

TABLE 2

| Compound ID | Fold increase adjusted for MW (compared to parent molecule |
|---|---|
| NaR | 1.0 |
| I-002 | 1.34 |
| I-003 | 1.76 |

Equivalents

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A salt selected from the group consisting of:

(S)-2-Ammonio-3-phenylpropanoate compound with 1-((2R,3R,4S,5R)-3,4-dihydroxy-5-(hydroxymethyl) tetrahydrofuran-2-yl)pyridine-1-ium-3-carboxylate (1:1) (I-001);

(2S,3S)-2-Ammonio-3-methylpentanoate compound with 1-((2R,3R,4S,5R)-3,4-dihydroxy-5-(hydroxymethyl) tetrahydrofuran-2-yl)pyridine-1-ium-3-carboxylate (1:1) (I-002);

(S)-2-Ammonio-3-(1H-indol-3-yl)propanoate compound with 1-((2R,3R,4S,5R)-3,4-dihydroxy-5-(hydroxymethyl)tetrahydrofuran-2-yl)pyridine-1-ium-3-carboxylate (1:1) (I-003);

1-((2R,3R,4S,5R)-3,4-dihydroxy-5-(hydroxymethyl)tetrahydrofuran-2-yl)pyridin-1-ium-3-carboxylate-(S)-6-amino-2-ammoniohexanoate (1:1) (I-004);

1-((2R,3R,4S,5R)-3,4-dihydroxy-5-(hydroxymethyl)tetrahydrofuran-2-yl)pyridin-1-ium-3-carboxylate (S)-5-amino-2-ammonio-5-oxopentanoate (1:1) (I-005);

1-((2R,3R,4S,5R)-3,4-dihydroxy-5-(hydroxymethyl)tetrahydrofuran-2-yl)pyridin-1-ium-3-carboxylate-(S)-2-ammonio-4-methylpentanoate (1:1) (I-006);

1-((2R,3R,4S,5R)-3,4-dihydroxy-5-(hydroxymethyl)tetrahydrofuran-2-yl)pyridin-1-ium-3-carboxylate-(S)-2-ammonio-4-carboxybutanoate (1:1) (I-007);

(S)-2-ammonio-3-methylbutanoate-1-((2R,3R,4S,5R)-3,4-dihydroxy-5-(hydroxymethyl)tetrahydrofuran-2-yl) pyridin-1-ium-3-carboxylate (1:1) (I-008);

(S)-2-ammonio-5-guanidinopentanoate-1-((2R,3R,4S,5R)-3,4-dihydroxy-5-(hydroxymethyl)tetrahydrofuran-2-yl)pyridin-1-ium-3-carboxylate (1:1) (I-009); and 1-((2R,3R,4S,5R)-3,4-dihydroxy-5-(hydroxymethyl)tetrahydrofuran-2-yl)pyridin-1-ium-3-carboxylate-(S)-2-ammonio-3-(1H-imidazol-4-yl)propanoate (1:1) (I-010).

2. A pharmaceutical composition comprising a salt of claim 1, and a pharmaceutically acceptable carrier.

3. The salt of claim 1, that is (S)-2-Ammonio-3-phenylpropanoate compound with 1-((2R,3R,4S,5R)-3,4-dihydroxy-5-(hydroxymethyl)tetrahydrofuran-2-yl)pyridine-1-ium-3-carboxylate (1:1) (I-001).

4. The salt of claim 1, that is (2S,3S)-2-Ammonio-3-methylpentanoate compound with 1-((2R,3R,4S,5R)-3,4-dihydroxy-5-(hydroxymethyl) tetrahydrofuran-2-yl)pyridine-1-ium-3-carboxylate (1:1) (I-002).

5. The salt of claim 1, that is (S)-2-Ammonio-3-(1H-indol-3-yl)propanoate compound with 1-((2R,3R,4S,5R)-3,4-dihydroxy-5-(hydroxymethyl)tetrahydrofuran-2-yl)pyridine-1-ium-3-carboxylate (1:1) (I-003).

6. The salt of claim 1, that is 1-((2R,3R,4S,5R)-3,4-dihydroxy-5-(hydroxymethyl)tetrahydrofuran-2-yl)pyridin-1-ium-3-carboxylate-(S)-6-amino-2-ammoniohexanoate (1:1) (I-004).

7. The salt of claim 1, that is 1-((2R,3R,4S,5R)-3,4-dihydroxy-5-(hydroxymethyl)tetrahydrofuran-2-yl)pyridin-1-ium-3-carboxylate (S)-5-amino-2-ammonio-5-oxopentanoate (1:1) (I-005).

8. The salt of claim 1, that is 1-((2R,3R,4S,5R)-3,4-dihydroxy-5-(hydroxymethyl)tetrahydrofuran-2-yl)pyridin-1-ium-3-carboxylate-(S)-2-ammonio-4-methylpentanoate (1:1) (I-006).

9. The salt of claim 1, that is 1-((2R,3R,4S,5R)-3,4-dihydroxy-5-(hydroxymethyl)tetrahydrofuran-2-yl)pyridin-1-ium-3-carboxylate-(S)-2-ammonio-4-carboxybutanoate (1:1) (I-007).

10. The salt of claim 1, that is (S)-2-ammonio-3-methylbutanoate-1-((2R,3R,4S,5R)-3,4-dihydroxy-5-(hydroxymethyl)tetrahydrofuran-2-yl) pyridin-1-ium-3-carboxylate (1:1) (I-008).

11. The salt of claim 1, that is (S)-2-ammonio-5-guanidinopentanoate-1-((2R,3R,4S,5R)-3,4-dihydroxy-5-(hydroxymethyl)tetrahydrofuran-2-yl)pyridin-1-ium-3-carboxylate (1:1) (I-009).

12. The salt of claim 1, that is 1-((2R,3R,4S,5R)-3,4-dihydroxy-5-(hydroxymethyl)tetrahydrofuran-2-yl)pyridin-1-ium-3-carboxylate-(S)-2-ammonio-3-(1H-imidazol-4-yl)propanoate (1:1) (I-010).

13. A cell culture medium for in vitro fertilization comprising:

a compound of claim 1; and culturing agents.

14. The cell culture medium of claim 13, wherein the culturing agent is an inorganic salt, an energy substrate, an amino acid, a chelator, a pH indicator, an antibiotic, a serum, a vitamin, a growth factor, or any combination thereof.

15. A method of treating an age-related infertility comprising administering to a subject in need thereof an effective amount of a salt of claim 1.

16. A method of treating infertility comprising administering to a subject in need thereof an effective amount of a salt of claim 1.

17. A method of improving oocyte or blastocyst quality and maturation comprising contacting the oocyte or blastocyst with an effective amount of a salt of claim 1 prior to implantation into a subject in need of treatment of age-related infertility.

18. The method of claim 17, wherein the oocyte or blastocyst is cultured in an IVF media containing the salt.

* * * * *